US011306361B2

(12) United States Patent
Bienvenu

(10) Patent No.: US 11,306,361 B2
(45) Date of Patent: Apr. 19, 2022

(54) PATHOLOGY PROGNOSIS METHOD

(71) Applicants: CENTRE NATIONAL DE LA RECHERCHE SCIENTIFIQUE, Paris (FR); UNIVERSITE DE MONTPELLIER, Montpellier (FR); AXLR, SATT DU LANGUEDOC ROUSSILLON, Montpellier (FR); INSTITUT NATIONAL DE LA SANTE ET DE LA RECHERCHE MEDICALE (INSERM), Paris (FR)

(72) Inventor: Frederic Bienvenu, Saint-Clement-de-Riviere (FR)

( * ) Notice: Subject to any disclaimer, the term of this patent is extended or adjusted under 35 U.S.C. 154(b) by 389 days.

(21) Appl. No.: 15/744,659

(22) PCT Filed: Jul. 18, 2016

(86) PCT No.: PCT/FR2016/051838
§ 371 (c)(1),
(2) Date: Jan. 12, 2018

(87) PCT Pub. No.: WO2017/009588
PCT Pub. Date: Jan. 19, 2017

(65) Prior Publication Data
US 2018/0202002 A1 Jul. 19, 2018

(30) Foreign Application Priority Data
Jul. 16, 2015 (FR) .................................... 1556731

(51) Int. Cl.
*C12Q 1/6886* (2018.01)
*C12Q 1/6883* (2018.01)
*C12Q 1/6818* (2018.01)

(52) U.S. Cl.
CPC ......... *C12Q 1/6886* (2013.01); *C12Q 1/6818* (2013.01); *C12Q 1/6883* (2013.01); *C12Q 2600/106* (2013.01); *C12Q 2600/118* (2013.01); *C12Q 2600/156* (2013.01); *C12Q 2600/158* (2013.01); *C12Q 2600/166* (2013.01); *C12Q 2600/178* (2013.01)

(58) Field of Classification Search
None
See application file for complete search history.

(56) References Cited

U.S. PATENT DOCUMENTS

2012/0252856 A1* 10/2012 Joy ..................... C12Q 1/6886
514/393

FOREIGN PATENT DOCUMENTS

WO 2006/059952 A1 6/2006

OTHER PUBLICATIONS

Terrinoni, A. et al. Genes, Chromosomes & Cancer 31:209-220. (Year: 2001).*

(Continued)

*Primary Examiner* — Diana B Johannsen
(74) *Attorney, Agent, or Firm* — Nixon & Vanderhye

(57) ABSTRACT

The invention relates to a method for the prognosis a person's susceptibility to environmental stress. The method includes: a step of determining the sequence for initiating the translation of at least one of the genes from the CCND family, and a step of quantifying the expression of the protein encoded by said gene, the translation initiation sequence of which was sequenced in the previous step, and comparing said expression with the expression level of said protein from a reference sample.

2 Claims, 15 Drawing Sheets

Specification includes a Sequence Listing.

(56) References Cited

OTHER PUBLICATIONS

Park, B.L. et al. Journal of Human Genetics 49:449-454. (Year: 2004).*
Li, Z. et al. Cancer Letters 354:77-86. (Year: 2014).*
Ho-Pun-Cheung, A. et al. PLoS One 7(7):e37065. (Year: 2012).*
Almendral J M et al: "Cloning and Sequence of the Human Nuclear Protein Cyclin: Homology With DNA-Binding Proteins", Proceedings of the National Academy of Sciences, National Academy of Sciences, US, vol. 84, Mar. 1, 1987 (Mar. 1, 1987), pp. 1575-1579, XP002952108, ISSN: 0027-8424, DOI: 10.1073/PNAS.84.6.1575.
Veira J et al: "The pUC plasmids, an M13mp7-derived system for insertion mutagenesis and sequencing with synthetic universal primers", Gene, Elsevier, Amsterdam, NL, vol. 19, No. 3, Oct. 1, 1982 (Oct. 1, 1982), pp. 259-268, XP023539775, ISSN: 0378-1119, [retrieved on Oct. 1, 1982], DOI: 10.1016/0378-1119(82)90015-4.
Tanioka M et al: "Transcriptional CCND1 expression as a predictor of poor response to neoadjuvant chemotherapy with trastuzumab in HER2-positive/ER-positive breast cancer", Breast Cancer Research and Treatment, Springer , NY, US, vol. 147, No. 3, Sep. 9, 2014 (Sep. 9, 2014), pp. 513-525, XP035396750, ISSN: 0167-6806, [retrieved on Sep. 9, 2014], DOI: 10.1007/S10549-014-3121-5.
Ashton Katie A et al: "The influence of the Cyclin D1 870 G>A polymorphism as an endometrial cancer risk factor", BMC Cancer, Biomed Central, London, GB, vol. 8, No. 1, Sep. 29, 2008 (Sep. 29, 2008), pp. 272, XP021042910, ISSN: 1471-2407, DOI: 10.1186/1471-2407-8-272.
Cheng Gang et al: "Overexpression of cyclin D1 in meningioma is associated with malignancy grade and causes abnormalities in apoptosis, invasion and cell cycle progression", Medical Oncology, Science and Technology Letters, Northwood, GB, vol. 32, No. 1, Dec. 13, 2014 (Dec. 13. 2014), pp. 1-8, XP035430305, ISSN: 1357-0560, [retrieved on Dec. 13, 2014], DOI: 10.1007/S12032-014-0439-0.
Yong Guo et al: "Let-7b expression determines response to chemotherapy through the regulation of Cyclin D1 in Glioblastoma", Journal of Experimental & Clinical Cancer Research, Biomed Central Ltd, London UK, vol. 32, No. 1, Jun. 27, 2013 (Jun. 27, 2013), pp. 41, XP021157291, ISSN: 1756-9966, DOI: 10.1186/1756-9966-32-41.
Frederic Bienvenu et al.: "Transcriptional role of cyclin D1 in development revealed by a "genetic-proteomic" screen", NIH Public Access, Author Manuscript Nature. Author manuscript; available in PMC Sep. 22, 2010, Nature. Jan. 21, 2010; 463(7279): 374 378.
Bradley C. Carthon et al.: "Genetic Replacement of Cyclin D1 Function in Mouse Development by Cyclin D2", Molecular and Cellular Biology, Feb. 2005, p. 1081-1088, vol. 25, No. 3, Returned for modification Aug. 19, 2004/Accepted Oct. 18, 2004.
Yan Geng et al.: "Rescue of Cyclin D1 Deficiency by Knockin Cyclin E", Cell, vol. 97, 767-777, Jun. 11, 1999, Replacement of Cyclin D1 by Cyclin E.
International Search Report, dated Oct. 24, 2016, from corresponding PCT/FR2016/051838 application.
Sabir et al., "Significance of cyclin D1 polymorphisms in patients with head and neck cancer," Int. J. Biol. Markers, 2013; 28(1): 49-55.

* cited by examiner

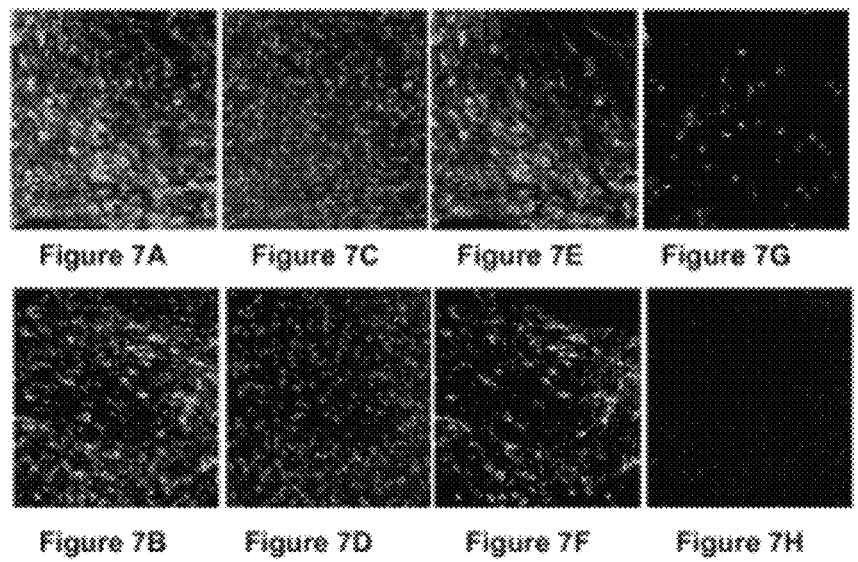
Figure 7A  Figure 7C  Figure 7E  Figure 7G
Figure 7B  Figure 7D  Figure 7F  Figure 7H
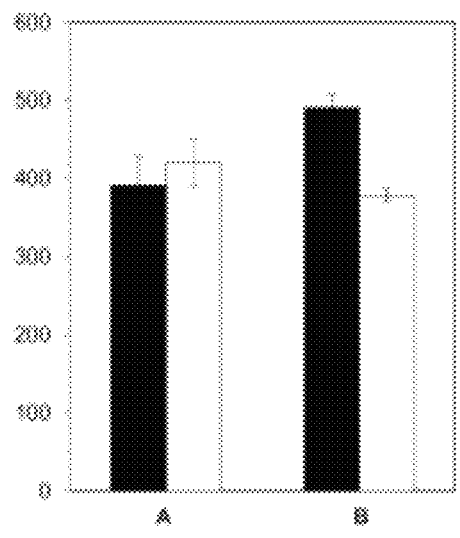
Figure 8

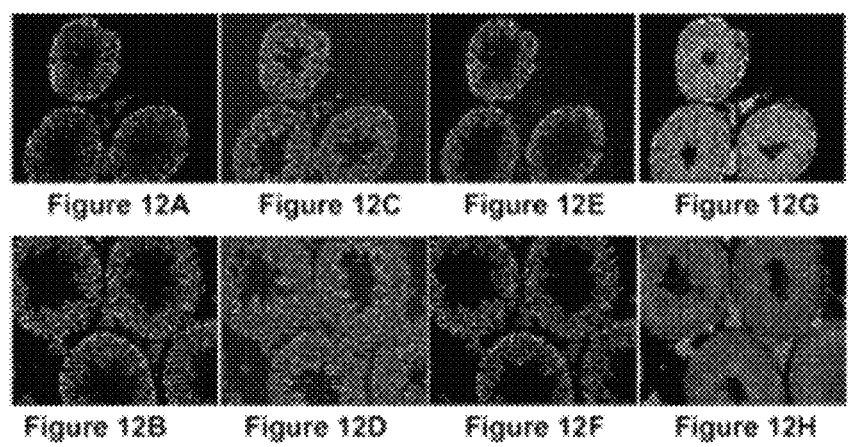
Figure 12A   Figure 12C   Figure 12E   Figure 12G
Figure 12B   Figure 12D   Figure 12F   Figure 12H
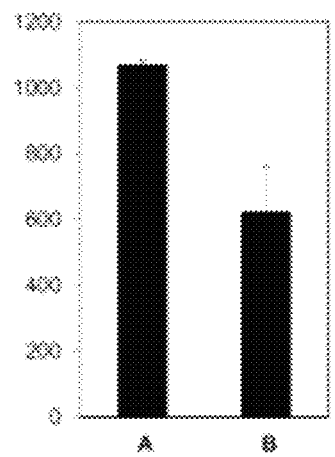
Figure 13

Figure 20
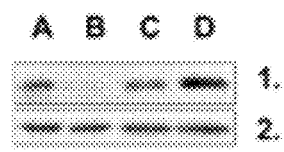
Figure 21
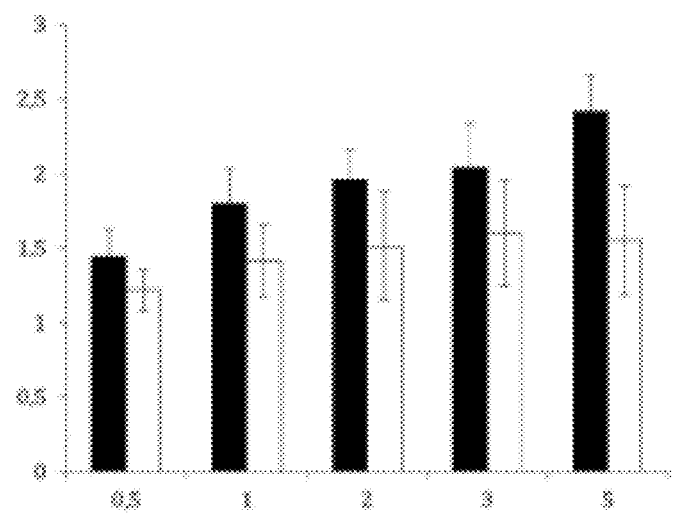
Figure 22

PATHOLOGY PROGNOSIS METHOD

The present invention relates to a method for the prognosis of pathologies.

Cyclin D1 is one of the components of the machinery of the cell cycle during development, but appears not to be essential for adult life.

During development, D Cyclins (Cyclins D1, D2 and D3) are at the heart of the integration of extracellular myogenic signals. To orchestrate the G1 phase of the cell cycle and support the entry into the S phase, the D Cyclins may promote the phosphorylation of RB or the proteins in the RB family (pocket proteins) through the activation of kinases dependent on CDK4/6 Cyclins, standardize the regulators of the cell cycle in the CDKN1 family to make it possible to adjust the E/CDK2 Cyclins' activity, and influence gene transcription by interacting with promoters.

Due to the plasticity of the cell cycle, the invalidation of the three genes coding the D Cyclins does not formally inhibit cell division. Indeed, most of the Cyclins involved in the cell cycle have redundant activities, but what matters is the tissue expression. Consequently, the invalidation of a single gene coding one of the 3D Cyclins prevents correct and complete development.

Interestingly, the CCND1 gene, which codes Cyclin D1, is the second most strongly altered gene in cancers in humans. Indeed, a strong expression of Cyclin D1 is found in a majority of cancers, and in particular breast carcinomas, which reinforces the oncogenic function of the CCN1 gene. Consequently, Cyclin D1 becomes a favored therapeutic target to treat cancer.

Indeed, the studies done in mice invalidated for the CCND1 gene (CCND1-/- not expressing Cyclin D1) have shown that females are protected from breast tumors caused by the ErbB2 or Ras oncogenes, probably due to the absence of CDK4 activity.

The conditional invalidation of Cyclin D1 in adult mice suggests its involvement in the development of ErbB2-dependent tumors.

However, the absence of CDK4 activation by Cyclin D1 leads to a decrease in progenitor mammary cells in adult mice after several gestations.

Consequently, to determine whether Cyclin D1 is a true candidate as a therapeutic target for cancer, it remains to determine whether Cyclin D1 has functions in adult organs and whether the invalidation of Cyclin D1 has therapeutic potential in tumors. The same remark applies to Cyclins D2 and D3.

In particular, the impact of Cyclin D1 in the prognosis for response to treatments for cancer patients remains to be determined.

One of the aims of the invention is to resolve this problem.

Another aim of the invention is to propose a reliable method for the prognosis of susceptibility to various environmental stresses.

Still another aim of the invention is to provide treatments suitable for certain tumors involving Cyclin D1.

Consequently, the invention relates to a prognosis method, in particular in vitro, for a person's susceptibility to an environmental stress, the method comprising:
a. a step for determining the translation initiation sequence, or KOZAK sequence, at least one of the genes in the Cyclin D family, CCND1, CCND2, CCND3, CCNE1 and CCNE2, from a biological sample from said individual, and comparison with a corresponding reference sequence to identify mutations,
b. a step for quantifying the expression of the protein coded by said gene whose KOZAK sequence was sequenced in the previous step, and comparison with the expression level of said protein derived from a reference sample, such that if the KOZAK sequence comprises a mutation and the expression level of the protein is modified relative to the reference level, said individual will be likelier to develop a pathology related to environmental stress.

The invention is based on the surprising observation made by the inventors that the quantity of Cyclin D1 has an impact on cell response to environmental stress. Furthermore, the inventors have identified that certain mutations in the messenger RNA sequence of Cyclin D1, Cyclin D2 or Cyclin D3, or Cyclin E1 or Cyclin E2, can affect the translation of the protein. In other words, mutations exist in the sequence of the gene coding Cyclin D1, or that coding Cyclin D2 or that coding Cyclin D3, or coding Cyclin E1 or coding Cyclin E2, which do not modify the expression level of the messenger RNAs, do not alter the function of the protein, but interfere with the protein translation and therefore the final quantity of protein.

An environmental stress refers to exposure to a harmful environmental condition or a toxic substance. Environmental stress results in endangering the cell integrity at the risk of leading to cell death, for example through breaks in the DNA, the generation of oxidizing reactive entities or a disruption in the potential of the membranes.

These mutations, which interfere with the translation into protein of the messenger RNAs of Cyclin D1, Cyclin D2 and Cyclin D3, and Cyclins E1 and E2, are mutations located in the translation initiation sequence, also called KOZAK or Kozak sequence. The Kozak sequence is a preserved sequence that one finds on eukaryotic messenger RNAs at the initiation site of the translation, around the ATG initiation codon (or AUG if the codon is read on an RNA sequence). In vertebrates, the Kozak sequence has, as consensus, gccRccAUGG, where R represents a purine (the initiation codon is underlined and the nucleotides in lowercase letters are preserved less than the rest of the sequence).

It is shown that the mutations in this region, which may be substitutions (i.e., the change of one nucleotide by another), insertions of at least one nucleotide or deletions of at least one nucleotide, can have a positive or negative effect on the translation.

A positive effect on the translation refers to a mutation that results in increasing the translation relative to the same sequence not having the mutation, the increase being at least 10%. From there, it will be considered that a mutation has a positive effect if its presence in a Kozak sequence leads to a 15% increase in the quantity of protein relative to the quantity of protein obtained with the Kozak sequence not having said mutation.

A negative effect on translation refers to a mutation that results in decreasing the translation relative to the same sequence not having the mutation, the decrease being at least 10%. It will then be considered that a mutation has a negative effect if its presence in a Kozak sequence leads to a 15% decrease in the quantity of protein relative to the quantity of protein obtained with the Kozak sequence not having said mutation.

In light of these elements, it will be understood that the method according to the invention requires two steps:
a step for characterizing the mutation, i.e., a step that identifies the difference in sequence relative to the reference sequence, and a step for measuring the level of expression of proteins coded by nucleic acid molecules having said mutation, relative to the protein level of the same molecule of nucleic acids not having said mutation.

Step for characterizing the mutation.

The step for characterizing the mutation in a Kozak sequence of a messenger RNA coding a protein from the Cyclin D family is an easy technique for one skilled in the art.

Among all of the methods known to date, one skilled in the art can use:

The SSCP, or single-strand conformation polymorphism, technique: this is a technique seeking to separate various alleles of the same gene (allozyme) by betting on the difference in migration in a gel not distorting their various conformations, the DGGE, or denaturing gradient gel electrophoresis, technique: this is an electrophoresis technique making it possible to separate molecules from nucleic acids (DNA or RNA) with the same size. Its principle consists of depositing a sample of nucleic acid on an electrophoresis gel containing a denaturing agent. In a DGGE gel, the fragments of nucleic acid are subjected to different concentrations, with increasing denaturant. The two strands of DNA separate more or less quickly based on their composition in AT and GC bases (2 hydrogen bonds for AT versus 3 for GC). Two different molecules can have strands that will not separate at the same time and will therefore migrate differently. The most stable molecule will migrate less quickly than that which will become denatured in the gradient.

the FAMA (fluorescence-assisted mismatch analysis) technique, derived from the chemical cleavage technique, which, by objectifying mismatches of pairs of heterologous (heteroduplex) DNA strands marked at their ends by different fluorophores, allows rapid exploration of a gene, or polymerization chain reaction, associated with sequencing.

Depending on the sequences, one skilled in the art will be capable of determining the most appropriate method, even if the most advantageous method is the PCR technique coupled with sequencing.

In the context of the PCR technique coupled with sequencing, one skilled in the art will easily determine a pair of oligonucleotides framing the region to be amplified (surrounding the Kozak sequence in which the presence of a mutation is suspected) and at least one nucleotide allowing the sequencing of the amplified region. The sequence techniques are very well known from the state of the art, and do not require further explanation.

Once the sequence is obtained, it is compared to a reference sequence that is a sequence not including a mutation. The reference sequence corresponds to the sequence primarily found in the general population, in the majority of healthy individuals, or not carrying the disease for which a prognosis or diagnosis is sought.

If the two sequences are identical, in this case it will be considered that the studied sequence is not a mutated sequence. The continuation of the method will therefore not be applied. If, however, the studied sequence differs by at least one nucleotide from the reference sequence, in this case it will be necessary to determine whether this so-called mutated sequence leads to the expression of a different quantity of protein, relative to the quantity of protein obtained with the reference sequence, not mutated.

Step for measuring the expression level of the protein downstream from the mutated Kozak sequence.

In order to determine whether the mutated sequence has a positive effect or a negative effect on translation, it is next necessary to measure the protein expression level of a protein placed downstream, or in position 3', from the Kozak sequence in which a mutation has been found.

Several methods can be considered:

it is for example possible to clone the mutated sequence upstream from a reporter protein, the expression of which may be measured, and quantified simply. For example, as reporter protein, we consider an autofluorescent molecule from the family of fluorescent proteins, such as GFP, RFP, CFP or YFP and derivatives thereof, the luciole luciferase protein, a protein having at least one tag of the MYC, HA, HIS, V5, VSVG, etc. type, or directly measuring the expression of the protein from the Cyclins D or E1 or E2 family whose gene has the mutation of the Kozak sequence identified in the preceding step (for example, see Example 2).

In the first example above, the measurement of the expression and quantification will be done based on the type of protein expressed under the control of the mutated Kozak sequence. For example, for the fluorescent proteins, the expression level may be measured by flux cytometry, in the case of luciferase, the expression level may be measured by spectrophotometry. For the tagged proteins, detection by immunoblot (or Western blot) is considered, or the technique described below.

In the case of direct measurement of the expression of proteins from the Cyclin D family, detection may be done by immunoblot, like for the tagged proteins, or by TR-FRET.

Indeed, the inventors have shown that if one uses two antibodies against Cyclin D1 and that are able to allow FRET, it is possible to quantify the quantity of Cyclin D1 protein reliably, specifically and reproducibly.

The TR-FRET method uses at least one pair of antibodies (i.e., at least two antibodies) against the same Cyclin D1 protein, each of the antibodies being coupled with a luminescent molecule. The luminescence may be defined as an emission of light (photons) by a luminescent molecule (fluorophore, enzyme, etc.). Among the luminescence phenomena, a distinction is made between photoluminescence (fluorescence, phosphorescence), which is subsequent to light excitation, chemiluminescence, for which the emission of light follows a chemical reaction, and bioluminescence, which is triggered by an enzymatic reaction.

When two luminescent molecules (respectively called the energy donor and acceptor) are close by, an energy transfer (RET) may occur from the donor to the acceptor. This phenomenon results in the complete extinction of the luminescence (fluorescence, bioluminescence, chemiluminescence) of the donor and the appearance of a fluorescence emission of the acceptor. This energy transfer is done with no light emission.

For this reason, and in order to perform an energy transfer between the first luminescent molecule and the second luminescent molecule, the first antibody is called donor antibody, since it has a first luminescent molecule which, after excitation, will transmit its energy to the second luminescent molecule carried by the antibody, which will be called acceptor antibody.

It is advantageous in the context of the inventive method for said donor and acceptor antibodies each to specifically recognize a different epitope of said protein coded by the CCND1 gene, so that they may concomitantly interact with said protein. Indeed, to obtain FRET (or an energy transfer), it is necessary for the luminescent molecules to be spatially close.

Consequently, advantageously, the donor and acceptor antibodies are capable of interacting with different epitopes, which are located on the same protein such that the luminescent molecules that they carry are especially close.

In the invention, it is specified that "said first and second luminescent molecules are such that the emission wavelength of the first luminescent molecule corresponds to the excitation wavelength of the second luminescent molecule". This means that in the presence of two energy donor-acceptor luminescent molecules (in particular fluorophores), the excitation phenomenon of the donor follows the process previously described, but its drop-out may, under certain conditions, go through a non-radiative energy transfer on the acceptor (and not through direct emission of a photon). The drop-out energy of the donor fluorophore is therefore "absorbed" by the acceptor fluorophore, which then goes from a fundamental state to an excited state. The return to the fundamental state of the acceptor can be done through an emission of a photon whose wavelength is greater than that of the photon that would have been emitted by the donor fluorophore without an acceptor.

The advantageous antibodies according to the invention are

- the cyclin D1 clone ab1 antibody, marketed by Thermofisher Scientific. This antibody corresponds to a monoclonal mouse antibody of type mouse IgG$_{2a/k}$, also called clone DCS-6, obtained by mouse immunization with the whole human Cyclin D1 protein,
- the Cyclin D1 clone ab3 antibody, marketed by Thermofisher Scientific. This is a polyclonal rabbit antibody obtained after immunization of the C-terminal part of the human Cyclin D1 protein.
- the Cyclin D1 clone SP4 antibody, marketed by Life Technologies, which recognizes the C-terminal epitope of the human Cyclin D1 protein, and directed against the peptide: QUIALLESSLRQAQQNMDPKAAEEEEEEEEEVDLACTPTDVRDVDI (SEQ ID NO: 4), and
- the Cyclin D1 clone 72-13G antibody, marketed by Santa Cruz Biotechnology Inc. under reference sc450. This antibody is a monoclonal mouse antibody against a murine Cyclin D1 fusion protein.

As mentioned above, the method according to the invention uses a donor antibody and at least one acceptor antibody. Consequently, in light of the four aforementioned advantageous antibodies, the method according to the invention covers the following 28 different combinations:

| Donor | Acceptor | Donor | Acceptor | Donor | Acceptor | Donor | Acceptor |
|---|---|---|---|---|---|---|---|
| ab1 | ab3 | ab3 | ab1 | SP4 | ab1 | sc450 | ab1 |
|  | SP4 |  | SP4 |  | ab3 |  | ab3 |
|  | SC450 |  | SC450 |  | SC450 |  | SP4 |
|  | ab3 + SP4 |  | ab1 + SP4 |  | ab1 + ab3 |  | ab1 + ab3 |
|  | ab3 + SC450 |  | ab1 + SC450 |  | ab1 + SC450 |  | ab1 + SP4 |
|  | SP4 + SC450 |  | SP4 + SC450 |  | ab3 + SC450 |  | ab3 + SP4 |
|  | ab3 + SP4 + SC450 |  | ab1 + SP4 + SC450 |  | ab1 + ab3 + SC450 |  | ab1 + ab3 + SP4 |

One of the advantageous combinations is the SC450 donor and ab1+ab3 acceptor combination.

In the context of the transfer of energy between two luminescent molecules, what is important is to have molecules whose excitation spectrum overlaps its emission spectrum the least. In other words, it is important for a same luminescent molecule as the emission spectrum at the excitation spectrum to overlap as little as possible, such that the excitation wavelength cannot correspond to the excitation wavelength of a second luminescent molecule that should be activated by energy transfer. In the case of an overlap, there is a lack of spectral specificity that is the source of significant background noise, which will greatly decrease the sensitivity of the quantification.

The development of luminescent molecules with similar properties has allowed considerable improvements to the spectral selectivity of pairs of organic fluorophores. The properties of these fluorophors make it possible to take FRET measurements in long time intervals (from several microseconds to a millisecond versus several nanoseconds for traditional fluorophores). This is why the term "time-resolved" (TR), or temporal selectivity, is used for the RET techniques using these molecules.

Rare earth cryptates are complexes formed from a macrolide (cryptate) forming a cage trapping a lanthanide atom.

An example lanthanide is illustrated by the following formula I:

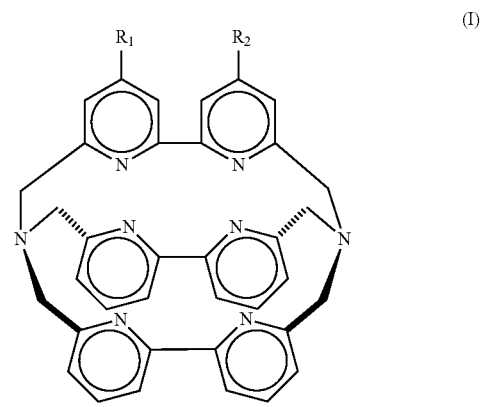

where R1 and R2 are reactive groups that make it possible to graft the cryptate on biomolecules, and in particular the antibodies.

One interesting property of cryptates lies in their ability to collect the energy from the photons of an exciting light source and transfer it to the lanthanide cation. This phenomenon is called antenna effect.

Furthermore, the lanthanide cryptates are particularly interesting because their excitation wavelength is in the ultraviolet (280 to 360 nm), while their emission wavelength is in the green-red (450 to 800 nm).

Still another advantage of lanthanide cryptates is their capacity for long fluorescence, i.e., after excitation, they continue to emit for lengths of time varying from microseconds to milliseconds, while the traditional fluorophores emit for several nanoseconds.

More particularly, the second luminescent molecule is advantageously d2, DY647, Cy5, Alexa647, or any other fluorophore emitting in the red when the first luminescent molecule is europium cryptate. Due to its broader emission spectrum, terbium cryptate can also be coupled with a second luminescent molecule absorbing in the red (d2, DY647, Cy5, Alexa647), but also in the green (fluorescein and GFP fluorescent proteins). These lists are not limiting, and one skilled in the art may, with his general knowledge, determine the various first and second luminescent molecules to be combined to obtain an energy transfer.

The d2 molecule is known from the state of the art, and is in particular described in U.S. Pat. No. 7,091,348 B2.

Advantageously, the pairs used are as follows:
SC450 coupled with europium cryptate, and the donor antibody or antibodies are coupled with d2, DY647, Cy5, Alexa647 or any other luminescent molecule absorbing in the red.
SC450 coupled with terbium cryptate, and the donor antibody or antibodies are coupled with d2, DY647, Cy5, Alexa647 or any other luminescent molecule absorbing in the red, but also fluorescein and GFP fluorescent proteins, or any other luminescent absorbing in the green.

The experimental conditions to carry out the method according to the invention, i.e., the quantity of antibodies used, the markings, the exposure to excitation light, the detection time, etc., are within the reach of one skilled in the art, since it involves routine experimentation.

Once the quantity of protein is measured, in the context of proteins is expression whose translation is controlled by the mutated Kozak sequence, this level of expression is compared to that of the same protein, but whose expression is controlled by the same Kozak sequence not having the mutation.

If the expression level of the protein whose translation is controlled by the mutated sequence is equivalent, i.e., the same plus or minus 15%, to the level of expression of the same protein whose translation is controlled by the reference sequence, in this case the mutation will be considered silent.

If the expression level of the protein whose translation is controlled by the mutated sequence is at least 15% greater than the expression level of the same protein whose translation is controlled by the reference sequence, in this case the mutation will be considered a positive mutation, the effect of which is to increase the expression.

If the expression level of the protein whose translation is controlled by the mutated sequence is at least 15% less than the expression level of the same protein whose translation is controlled by the reference sequence, the mutation will be considered a negative mutation, the effect of which is to decrease the expression.

In the context of the inventive method, it is possible for a studied Kozak sequence to have more than one difference relative to the reference sequence, i.e., to have more than one mutation. In this case, it will be possible to determine the joint effect of the set of these mutations, but also to determine the individual effect of these mutations. To measure the individual effect, it will be possible to reconstitute each of the mutations artificially, for example by directed mutagenesis by using oligonucleotides carrying the mutation to be inserted into the reference sequence. These directed mutagenesis techniques are well known by those skilled in the art.

In one advantageous embodiment, the invention relates to a prognosis method as previously defined, in which if the expression level of the protein is higher than the reference expression level, said individual will have a greater chance of developing a tumor resistant to chemotherapy.

The inventors have shown that the mutations that have a positive effect are associated with a poor prognosis for response to chemotherapy. Consequently, if, in a patient sample, a mutation is identified with a positive effect, the patient should have a low response to chemotherapy, and additional treatment will be necessary to cause the tumor to regress and potentially lead to remission.

In the context of prognosis of resistance to chemotherapy, it is advantageous for the method to be applied to a tumor sample taken from a patient, i.e., from a biopsy for solid tumors, or a blood sample or bone marrow sample for leukemias and blood diseases.

In one advantageous embodiment, the invention relates to a prognosis method as previously defined, in which if the expression level of the protein is not as high as the reference expression level, said individual will have a greater chance of developing a neurodegenerative disease, a cardiac disease or infertility.

In the context of the prognosis of development of a neurodegenerative disease, a heart disease or infertility, in particular male infertility, it is advantageous for the method to be applied to a sample taken from an individual corresponding to the target organ of the disease. However, these mutations often being constitutional, the application of the method to a blood sample is also appropriate.

In another embodiment, the invention relates to a prognosis method as previously defined, in which the reference sequence of the KOZAK sequence:
of the CCND1 gene comprises the following sequence:
5'-AGA GCC CCA GCC ATG GAA CAC CAG CTC-3' 9SEQ ID NO: 1),
of the CCND2 gene comprises the following sequence:
5'-GCC GGG CTG GCC ATG GAG CTG CTG TGC-3' (SEQ ID NO: 2),
of the CCND1 gene comprises the following sequence:
5'-CGC TGC CCG AGT ATG GAG CTG CTG TGT-3' (SEQ ID NO: 3),
of the CCNE1 gene comprises the following sequence:
5'-AGC CCC ATC ATG CCG A-3' (SEQ ID NO: 47), and
of the CCNE2 gene comprises the following sequence:
5'-AAG AAG AGA ATG TCA AGA-3' (SEQ ID NO: 48).

When the Kozak reference sequence is considered from a messenger RNA, the latter is as follows:
5'-AGA GCC CCA GCC AUG GAA CAC CAG CUC-3' (SEQ ID NO: 5), for the Kozak sequence of the messenger RNA coding the Cyclin D1,
5'-GCC GGG CUG GCC AUG GAG CUG CUG UGC-3' (SEQ ID NO: 6), for the Kozak sequence of the messenger RNA coding the Cyclin D2,
5'-CGC UGC CCG AGU AUG GAG CUG CUG UGU-3' (SEQ ID NO: 7), for the Kozak sequence of the messenger RNA coding the Cyclin D3,
5'-AGC CCC AUC AUG CCG A-3' (SEQ ID NO: 49), for the Kozak sequence of the messenger RNA coding the Cyclin E1,
5'-AAG AAG AGA AUG UCA AGA-3' (SEQ ID NO: 50), for the Kozak sequence of the messenger RNA coding the Cyclin E2.

It is in fact advantageous to look for mutations in 5' and in 3' of the initiating codon. In the invention, the nucleotides of sequences a SEQ ID NO: 1, 2 and 3 will be numbered as follows. The A of the ATG initiator codon (or AUG if we are considering RNA) corresponds to position zero (0). The nucleotides in 5' (on the left) will be numbered negatively from A, and the nucleotides in 3' (on the right) will be numbered positively from A. Thus, to exemplify this nomenclature, in sequence SEQ ID NO: 1, the G nucleotide of the GCC codon will be in position −9 relative to the A of the ATG, and the T nucleotide of the CTC codon will be in position +13 relative to the A of the ATG.

It appears obvious for one skilled in the art that positions 0, +1 and +2, which correspond to the ATG codon, will not have to be mutated, failing which there will be no translation.

The aforementioned definitions apply mutatis mutandis to the sequences SEQ ID NO: 4, 5 and 6.

Advantageously, the invention relates to a prognosis method as defined above, in which the quantification of the expression of the protein coded by said gene whose KOZAK sequence was sequenced is done by FRET.

Advantageously, the invention relates to a prognosis method as defined above, in which the sequencing of said KOZAK sequence is done by PCR on the messenger RNA coded by said gene.

The invention further relates to a prognosis method, in particular in vitro, for resistance to chemotherapy of a tumor, said method comprising a step for detecting a mutation in the KOZAK sequence of the CCND1 gene, said mutation being a C→G substitution in position −7 relative to the ATG codon of the sequence SEQ ID NO: 1.

As shown below, the inventors have identified a mutation in position −7 relative to the ATG of the Kozak sequence of the gene coding the Cyclin D1, which results in increasing the expression of the protein. Consequently, the identification, in a patient with a tumor, of this substitution where the C of the reference sequence is substituted by a G, will be a poor prognosis. Indeed, due to the strong expression of the Cyclin D1 protein, the tumor will be resistant to chemotherapy treatment.

The invention additionally relates to a composition comprising a pair of oligonucleotides allowing sequencing of the KOZAK sequence of the gene coding the Cyclin D1, Cyclin D2 or Cyclin D3 protein, for use thereof in the context of the prognosis of resistance to chemotherapy of a tumor developed by an individual.

Advantageously, the following oligonucleotides can be used to obtain the sequence from the Kozak sequence:

```
CCND1: clockwise primer
                                       (SEQ ID NO: 38)
(5'-GGGCAGCAGAAGCGAGAG-3')

counterclockwise primer
                                       (SEQ ID NO: 39)
(5'-CGGTCGTTGAGGAGGTTG-3')

CCND2: clockwise primer
                                       (SEQ ID NO: 40)
(5'-TAGCCAAAGGAAGGAGGTCA-3')

counterclockwise primer
                                       (SEQ ID NO: 41)
(5'-AAGTAGGAGCACTGCGGAAG-3')

CCND3: clockwise primer
                                       (SEQ ID NO: 42)
(5'-ATTCCACGGTTGCTACATCG-3')

counterclockwise primer
                                       (SEQ ID NO: 43)
(5'-GCACGCACTGGAAGTAGGAG-3')

CCNE1: clockwise primer
                                       (SEQ ID NO: 51)
(5'-GGACAAGACCCTGGCCTC-3')

counterclockwise primer
                                       (SEQ ID NO: 52)
(5'-GTCCTGTCGATTTTGGCCAT-3')

CCNE2: clockwise primer
                                       (SEQ ID NO: 53)
(5'-CTTTGTTCCCGGAGCTGTTC-3')

counterclockwise primer
                                       (SEQ ID NO: 54)
(5'-TTTCCTCTTCTTGGCCTGGA-3')
```

The invention also relates to a composition comprising at least one interfering RNA directed against the CCND1 gene, coding the cyclin D1 protein, for its use in the context of the treatment of a chemotherapy-resistant tumor, the cells of said tumor comprising a mutation in the KOZAK sequence of the CCND1 gene, said mutation being a C→G substitution in position −7 relative to the ATG codon of sequence SEQ ID NO: 1.

The aforementioned mutated Kozak sequence is illustrated by the following sequence: 5'-AGA GCG CCA GCC ATG GAA CAC CAG CTC-3' (SEQ ID NO: 8).

As described above, the increased quantity of Cyclin D1 relative to the reference quantity results in making a tumor resistant to chemotherapy. Consequently, to treat said tumor effectively using chemotherapy, it is advantageous to try to reduce the quantity of Cyclin D1. To that end, the approach consisting of inhibiting the expression of the protein by using a small RNA able to produce the interference with the RNA is particularly advantageous.

Advantageously, at least one of the following 3 siRNAs can be used.

```
siRNA1
                                       (SEQ ID NO: 44)
(5'-GCC AGG ATG ATA AGT TCC TTT-3')

siRNA2
                                       (SEQ ID NO: 45)
(5'-ATT GGA ATA GCT TCT GGA AT-3')

siRNA3
                                       (SEQ ID NO: 46)
(5'-CCA CAG ATG TGA AGT TCA TTT-3')
```

Advantageously, the invention relates to an aforementioned composition for its aforementioned use, in combination with chemotherapy.

Advantageously, the composition according to the invention is used with any one of the following compounds, alone or in combination: cisplatin, oxaliplatin, paclitaxel, irinotecan (SN38) and 5-FluoroUracil.

The invention will be better understood upon reading the following figures and the example below.

LEGEND OF THE FIGURES

FIG. 1 shows a Western blot showing the expression of the wild Cyclin D1 (1.) in different organs: A: liver, B: kidney, C: lungs, D: heart, E: eye, F: ovaries, G: spleen; H: pancreas, I: brain. The extracts are normalized with actin (2.) and tubulin (3.).

FIG. 2 shows a Western blot showing the expression of the tagged Cyclin D1 FLAG-HA (1.) in different organs: A: lungs, B: kidney, C: liver, D: heart, E: testicles, F: eye, G: spleen, H: brain, I: pancreas. The extracts are normalized with actin (2.) and tubulin (3.).

FIG. 3 shows a Western blot showing the expression of the tagged Cyclin D1, revealed by the anti-HA antibody (1.) in two organs: A: male Ctag/Ctag mouse spleen, B: male Ntag/Ntag mouse spleen, C: male +/+ mouse spleen, D: female Ctag/Ctag mouse spleen, E: female Ntag/Ntag mouse spleen, F: female +/+ mouse liver, G: female Ctag/Ctag mouse liver, H: female Ntag/Ntag mouse liver, i.e.: male Ctag/Ctag mouse liver, and J: male Ntag/Ntag mouse liver. The extracts are normalized with tubulin (2.).

Figure 5A:
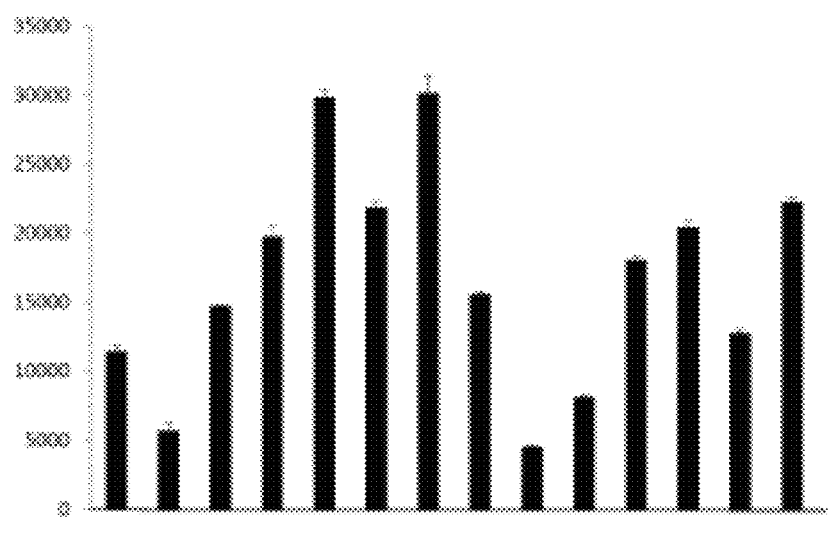
FIGS. 5A and 5B show that the HTRF signal can be enhanced by using several acceptors.

FIG. 5A shows a graph showing the HTRF signal obtained from cells expressing an N-terminal tagged Cyclin D1 for the following different "donor" "acceptor" combinations: A: anti-FLAG donor +anti-HA acceptor; B: anti-FLAG donor+ab1 acceptor; C: anti-FLAG donor+ab3 acceptor; D: anti-FLAG donor+anti-HA and ab1 acceptors; E: anti-FLAG donor+anti-HA and ab3 acceptors; F: anti-FLAG donor+ab1 and ab3 acceptors; G: anti-FLAG donor+ anti-HA and ab1 and ab3 acceptors; H: anti-HA donor+anti-FLAG acceptors; I: anti-HA donor+ab1 acceptors; J: anti-HA donor+ab3 acceptors; K: anti-HA donor+anti-FLAG and ab1 acceptors; L: anti-HA donor+anti-FLAG and ab3 acceptors; M: anti-HA donor+ab1 and ab3 acceptors, and N: anti-HA donor+anti-FLAG and ab1 and ab3 acceptors.

Figure 5B:
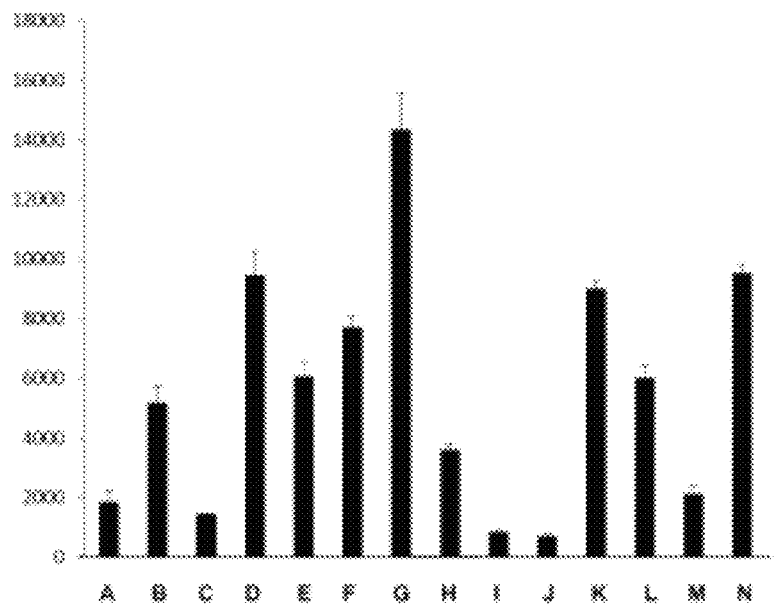

FIG. 5B shows a graph showing the HTRF signal obtained from cells expressing a C-terminal tagged Cyclin D1 for the following different "donor" "acceptor" combinations: A: anti-FLAG donor+anti-HA acceptor; B: anti-FLAG donor+ab1 acceptor; C: anti-FLAG donor+ab3 acceptors; D: anti-FLAG donor+anti-HA and ab1 acceptors; E: anti-FLAG donor+anti-HA and ab3 acceptors; F: anti-FLAG donor+ab1 and ab3 acceptors; G: anti-FLAG donor+ anti-HA and ab1 and ab3 acceptors; H: anti-HA donor+anti-FLAG acceptors; I: anti-HA donor+ab1 acceptors; J: anti-HA donor+ab3 acceptors; K: anti-HA donor+anti-FLAG and ab1 acceptors; L: anti-HA donor+anti-FLAG and ab3 acceptors; M: anti-HA donor+ab1 and ab3 acceptors, and an: anti-HA donor+anti-FLAG and ab1 and ab3 acceptors.

Figure 6:
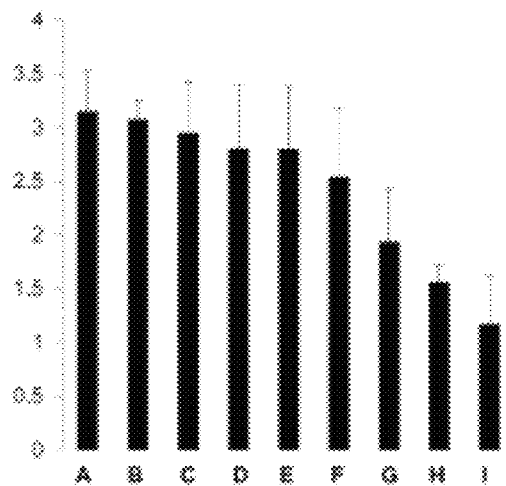

FIG. 6 is a graph showing the ratio of the quantity of C-terminal tagged Cyclin D1/the quantity of N-terminal tagged Cyclin D1, in different organs: A: brain, B: eye, C: lungs, D: kidney, E: heart, F: testicles, G: pancreas, H: spleen and I: liver.

FIGS. 7A to 7H correspond to immunofluorescence of Cyclin D1 in Substantia nigra pars compacta of adult mice.

FIG. 7A corresponds to the superposition of fluorescences obtained by marking the DNA with DAPI, tyrosine hydroxylase and the HA tag, in the $CCND1^{Ctag/Ctag}$ mouse substantia nigra.

FIG. 7B corresponds to the superposition of fluorescences obtained by marking of the DNA with DAPI, tyrosine hydroxylase and the HA tag, in the $CCND1^{+/+}$ mouse substantia nigra.

FIG. 7C corresponds to the marking of the DNA with DAPI in the $CCND1^{Ctag/Ctag}$ mouse substantia nigra.

FIG. 7D corresponds to the marking of the DNA with DAPI in the $CCND1^{+/+}$ mouse substantia nigra.

FIG. 7E corresponds to the marking of the tyrosine hydroxylase in the $CCND1^{+/+}$ mouse substantia nigra.

FIG. 7F corresponds to the marking of the HA tag, in the $CCND1^{Ctag/Ctag}$ mouse substantia nigra.

FIG. 7G corresponds to the marking of the HA tag, in the $CCND1^{Ctag/Ctag}$ mouse substantia nigra.

FIG. 7H corresponds to the marking of the HA tag, in the $CCND1^{+/+}$ mouse substantia nigra.

FIG. 8 shows a graph showing the HTRF signals (arbitrary units) obtained from the substantia nigra (B) and the striatum (A) of the $CCND1^{Ntag/Ntag}$ mouse 24 hours after an intraperitoneal injection of salt (black bars) or methamphetamine saline solution (white bars) at 5 mg/kg. The error bars represent the standard deviation over three independent experiments.

Figure 9:
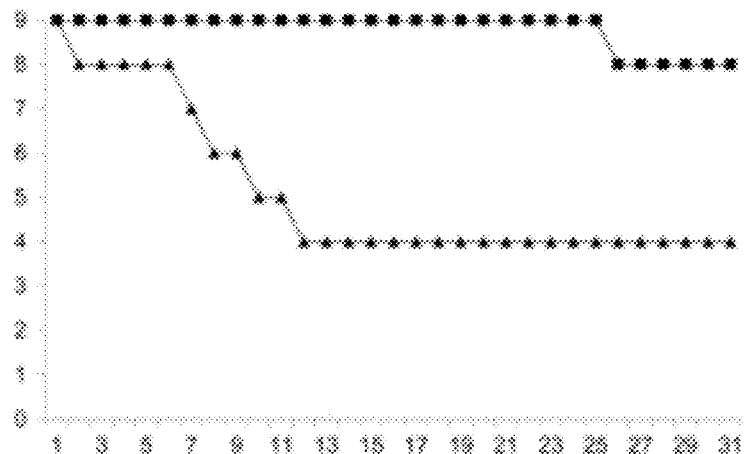

FIG. 9 is a Kaplan-Meyer survival curve for female mice expressing the N-terminal tagged Cyclin D1 (black triangles) compared to the survival of wild mice (black squares), after treatment with 6-hydroxydopamine.

Figures 10, 11:
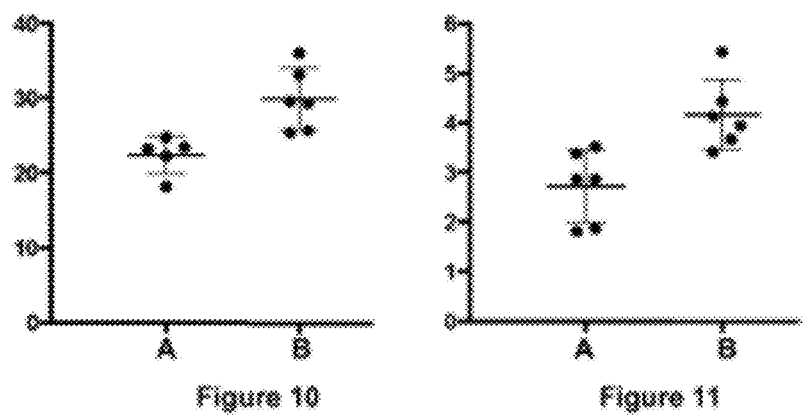

FIG. 10 is a graph showing the size of the myocardial infarction (percentage of the risk area) after ischemia and reperfusion in mice that are A: wild and B: expressing the N-terminal tagged Cyclin D1. Each point corresponds to a mouse.

FIG. 11 is a graph showing the fragmentation of the DNA (ratio of the apoptosis measurement of the ischemia region to the non-ischemic region in arbitrary units) after ischemia and reperfusion in mice that are A: wild and B: expressing N-terminal tagged Cyclin D1.

FIGS. 12A to 12H correspond to immunofluorescence of the Cyclin D1 in the testicles.

FIG. 12A corresponds to the superposition of the fluorescence obtained by marking the DNA with DAPI, TRA98 and the HA tag, in the testicles of $CCND1^{Ctag/Ctag}$ mice.

FIG. 12B corresponds to the superposition of the fluorescences obtained by marking the DNA with DAPI, TRA98 and the HA tag, in the testicles of $CCND1^{+/+}$ mice.

FIG. 12C corresponds to the marking of the DNA with DAPI in the testicles of $CCND1^{Ctag/Ctag}$ mice.

FIG. 12D corresponds to the marking of the DNA with DAPI in the testicles of $CCND1^{+/+}$ mice.

FIG. 12E corresponds to the marking of TRA98 in the testicles of $CCND1^{Ctag/Ctag}$ mice.

FIG. 12F corresponds to the marking of TRA98 in the testicles of $CCND1^{+/+}$ mice.

FIG. 12G corresponds to the marking of the HA tag, in the testicles of $CCND1^{Ctag/Ctag}$ mice.

FIG. 12H corresponds to the marking of the HA tag, in the testicles of $CCBD1^{+/+}$ mice.

FIG. 13 depicts a graph showing the HTRF signals (arbitrary units) obtained from the testicles of $CCND1^{Ntag/Ntag}$ mice 14 hours after an intraperitoneal injection of salt (A) or methoxyacetic acid saline solution at 150 mg/kg. The error bars show the standard deviation over three independent experiments.

Figure 14:

FIG. 14 depicts a Western blot showing the expression of the tagged Cyclin D1, revealed by the anti-FLAG antibody (1.) in MEF transformed with the mouse T antigen: A: without Cyclin D1 (−/−), B: of mice expressing N-terminal tagged Cyclin D1 (Ntag/Ntag) and C: in mice expressing the C-terminal tagged Cyclin D1 (Ctag/Ctag). The extracts are normalized with actin (2.).

Figure 15:
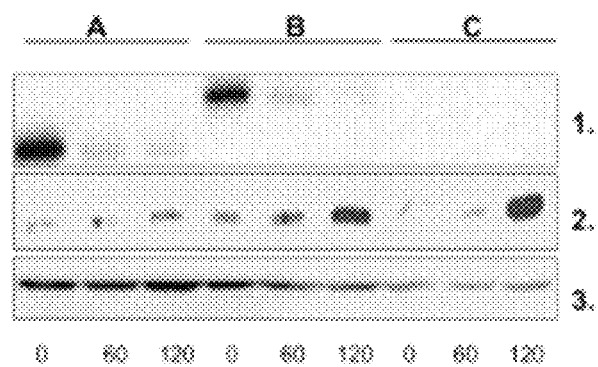

FIG. 15 shows a Western blot showing the expression of the Cyclin D1 (1.) in MEFs transformed with the mouse T antigen: A: wild (+/+), B: of mice expressing the N-terminal tagged Cyclin D1 (Ntag/Ntag), and C: mice not expressing Cyclin (−/−), treated with 0.5M of ethanol at the indicated times (in minutes). The quantity of cleaved PARP is also detected (2.). The quantity The extracts are normalized with actin (3.).

Figure 16:
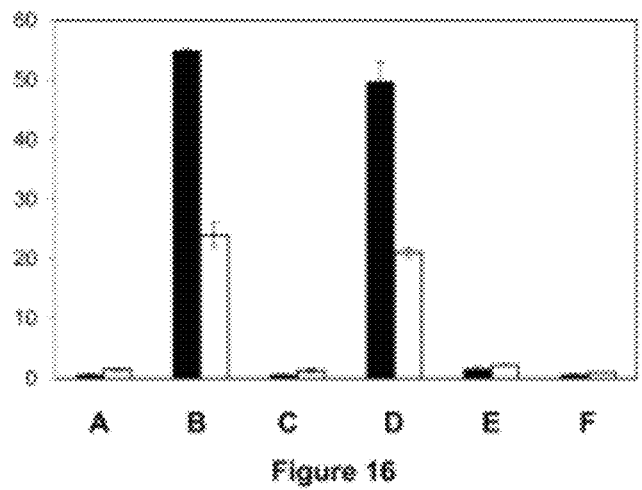

FIG. 16 is a graphic showing the percentage of apoptotic cells in the MEF cells immortalized with the T antigen derived from mice not expressing Cyclin D1 (−/−; black bars) or wild mice (+/+; white bars), after treatment A: with a saline solution, B: after treatment with actinomycin D (30 µM), C: after treatment with PD0332991 (100 nM), E: after treatment with actinomycin D (30 µM) and Q-VD-Oph (20 µM) and F: after treatment with Q-VD-Oph (20 µM).

Figure 17:
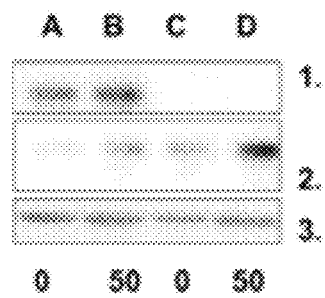

FIG. 17 shows a Western blot showing the expression of the Cyclin D1 (1.) in MEFs transformed with the mouse T antigen: A, B not expressing endogenous Cyclin (−/−) and expressing C-terminal tagged ectopic Cyclin D1 under the control of a mutated Kozak sequence, C, D: not expressing endogenous Cyclin (−/−), treated with (B, D) or without (A, C) 0.5M of ethanol. The quantity of cleaved PARP is also detected (2.). The quantity The extracts are normalized with the actin (3.).

Figure 18:
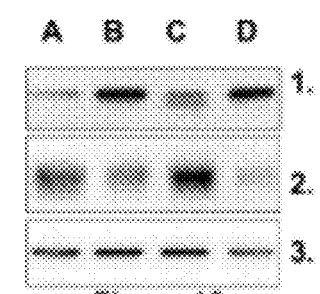

FIG. 18 illustrates a Western blot showing the expression of the Cyclin D1 (1.) in MEFs transformed with the mouse T antigen not expressing Cyclin (−/−) and expressing: A: the N-terminal tagged Cyclin D1 under the control of a mutated Kozak sequence, B: the N-terminal tagged Cyclin D1 under the control of a wild Kozak sequence, C: the C-terminal tagged Cyclin D1 under the control of a mutated Kozak sequence, and D: the C-terminal tagged Cyclin D1 under the control of a wild Kozak sequence. All of the cells are treated with ethanol at 0.5M for 120 min. The quantity of cleaved PARP is also detected (2.). The quantity The extracts are normalized with actin (3.).

Figure 19:
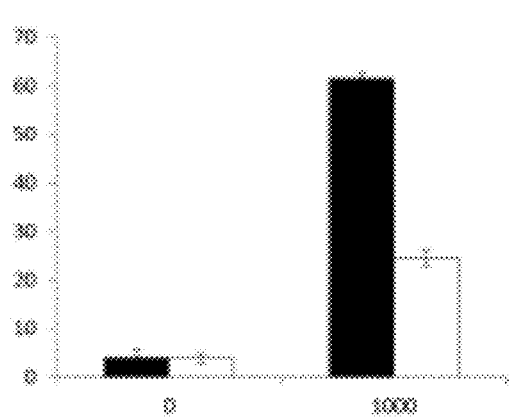

FIG. 19 is a graph depicting the data obtained by FACS of cell death in % as a function of the quantity of ethanol (0 or 1000 mM) on MEF −/− re-expressing the N-terminal tagged Cyclin D1 and the control of a mutated (black bars) or wild (white bars) Kozak sequence.

FIG. 20 is a schematic illustration of polymorphisms found in the Kozak sequence of the human CCND1 gene. The position of the polymorphisms is indicated by S or the M above the sequence SEQ ID NO: 35.

FIG. 21 shows a Western blot showing the fragmentation of the PARP (1.) in the MEFs transformed with the mouse T antigen not expressing Cyclin (−/−) and expressing: A and D: the C-terminal tagged human Cyclin D1 under the control of a wild Kozak sequence, B and C: the C-terminal tagged human Cyclin de under the control of a C/G mutated Kozak sequence in position −7. The cells are treated either with a nonrelevant siRNA (A and B) or with an anti-HA siRNA (C and D). All of the cells are treated with ethanol at 0.5M for 120 min. The quantity The extracts are normalized with actin (2.).

FIG. 22 is a graph showing the induction of apoptosis (arbitrary units) of MEF −/− cells expressing the human Cyclin D1 under the control of a mutated Kozak sequence (−7C/G; white bars) or under the control of a wild Kozak sequence (black bars) as a function of time (indicated on the X axis in hours) after treatment with 500 mM of ethanol.

Figure 23:
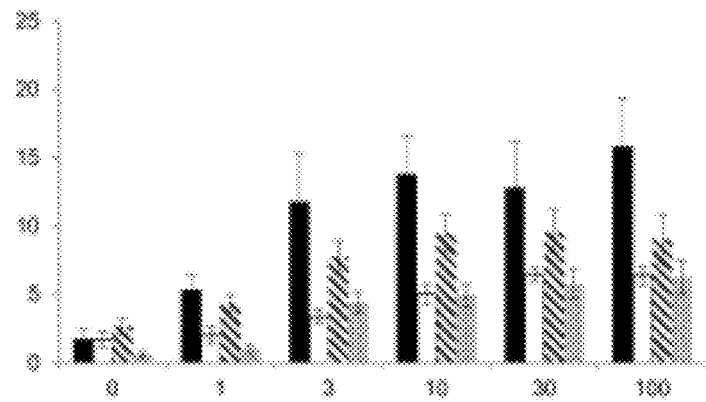

FIG. 23 is a graph showing the percentage of apoptotic cells after treatment with 5-FU, at the doses indicated on the X axis (in µM), of MEF cells transformed by RAS-G12VDNP53 not expressing Cyclin D1 (−/−; black bars), wild (white bars), expressing the N-terminal tagged Cyclin D1 under the control of an optimal Kozak sequence (bars with crosshatching) or expressing the C-terminal tagged Cyclin D1 under the control of a wild Kozak sequence (gray bars).

Figure 24:
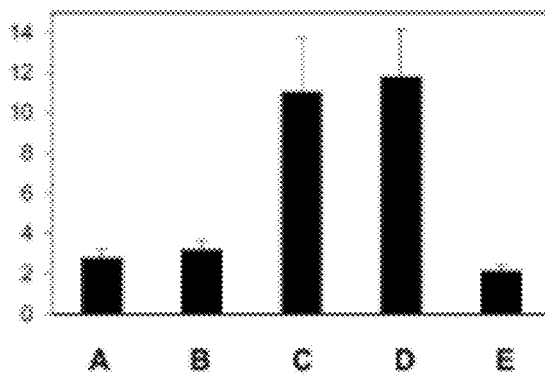

FIG. 24 is a graph showing the percentage of apoptotic cells after treatment of the transformed MEF cells with RAS-G12V/DNP53, A: not treated, B: treated with PD0332991 (500 nM), C: treated with 5-FU (100 µM), D: treated with 5-FU (100 µM) and PD0332991 (500 µM) and E: treated with 5-FU (100 µM) and Q-VD-Oph (20 µM).

Figure 25:
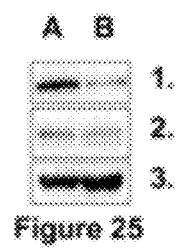

FIG. 25 is a Western blot showing the phosphorylation of RB in S780 (1.), the total quantity of RB (2.) on cells of FIG. 24 not treated (A) or treated with PD0332991 (B). The lysates are normalized with actin (3.).

Figure 26:

FIG. 26 is a Western blot showing the immunoprecipitation of the Cyclin D1 using the anti-HA antibody (A to C), anti-FLAG antibody (E to G), or with nonrelevant immunoglobulins (D and H) from cells derived from MMTV-ErbB2 mammary tumors after treatment for one minute with 1% paraformaldehyde, expressing N-terminal tagged Cyclin D1 (A, C to E and G to H) or normal Cyclin D1 (B and F). The caspase 3 is detected (1.), as well as the Cyclin D1 (2.).

Figure 27:
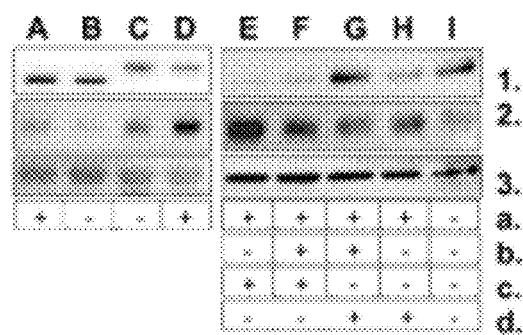

FIG. 27 is a Western blot detecting Cyclin D1 (1.) and the cleavage of the PARP (2.) from cells derived from MMTV-ErbB2 mammary tumors expressing the wild Cyclin D1 (A and B), expressing the N-terminal tagged Cyclin D1 (C to I), after treatment (+) or not (−) with the following drugs: 5-FU (100 µM; a.), Q-VD-Oph (20 µM; b.), a siRNA directed against the HA tag (c.) and a nonrelevant siRNA (d.). The charges are normalized with actin (3.).

Figure 28:
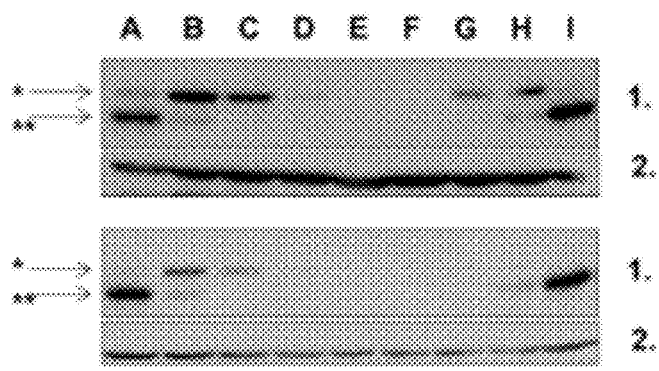

FIG. 28 is a Western blot showing the quantity of Cyclin D1 (1.), tagged (*) or not (**), in two clones (high and low) of MEFCCND1$^{-/-}$ cells expressing: A and I: the tagged Cyclin D1 protein and the T286A form of Cyclin D1, B and H: the tagged T286A form of Cyclin D1 and the cyclin D1 protein, CNG: the tagged T286A form of Cyclin D1, D and F: the tagged Cyclin D1 protein, E the MEF CCND1−/− cells. The cells were also treated with an anti-tag siRNA (F to I), where only the tagged form is sensitive to inhibition. The proteins are normalized with actin (2.).

Figure 29:
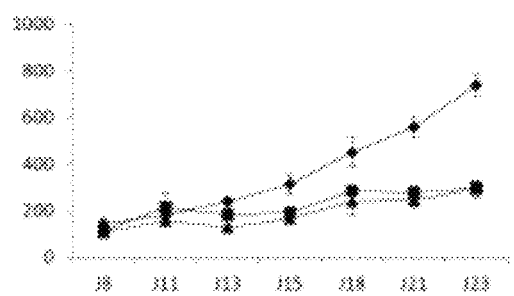

FIG. 29 is a graph showing the size of the tumors (in mm$^3$) as a function of time (indicated on the x-axis) obtained from a thymic mice (nude) injected with 3T3 cells transformed with the tagged T286A form of Cyclin D1, treated with a nonrelevant siRNA (curve with diamonds), with an anti-HA siRNA (curve with squares) or anti-FLAG (curve with triangles). The error bars correspond to the standard deviation over 10 tumors.

Figure 30:
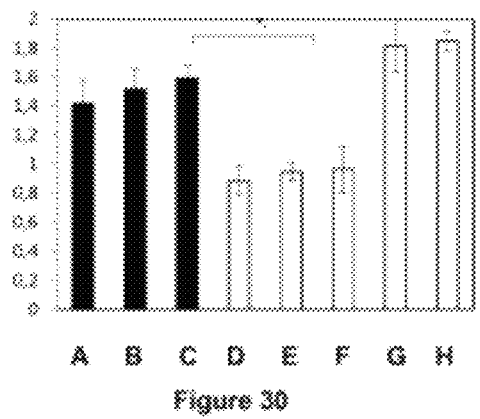

FIG. 30 is a graph showing the increase in the tumor 5 days after injection in nude mice of 3T3 cells expressing the T286A form of the Cyclin D1 (ATC) or the tagged T286A form of Cyclin D1 (D to H) after treatment with: A and D: an anti-HA siRNA, B and E: an anti-FLAG siRNA and an anti-HA siRNA, C and F: an anti-FLAG siRNA, G: a nonrelevant siRNA, and H without siRNA. The error bars correspond to the standard deviation of 10 tumors.

Figure 31:
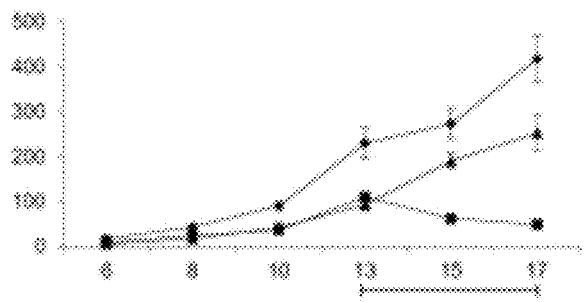

FIG. 31 is a graph showing the size of the tumors (in mm$^3$) over time (days) obtained from nude mice injected with MEF cells converted with RAS-G12V/DNP53 expressing Cyclin D1 and treated with an anti-HA siRNA (curve with diamonds), expressing the N-terminal tagged Cyclin D1 and treated with an anti-HA siRNA (curve with squares), or expressing the N-terminal tagged Cyclin D1 and treated with a nonrelevant siRNA (curve with triangles). The treatment with the siRNAs is indicated by the horizontal bar (Days 13 to 17).

Figure 32:
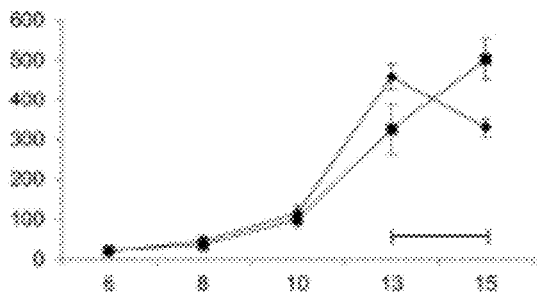

FIG. 32 is a graph showing the size of the tumors (in mm$^3$) over time (in days) obtained from nude mice injected with MEF cells transformed with RAS-G12V/DNP53 expressing the C-terminal tagged Cyclin D1 and treated with an anti-HA siRNA (curve with diamonds), or expressing the N-terminal tagged Cyclin D1 and treated with a nonrelevant siRNA (curve with squares). The treatment with siRNAs is indicated by the horizontal bar (Days 13 to 15).

FIGS. 33A to 33D show photos of tumors before and after treatment with a siRNA.

Figure 33A:
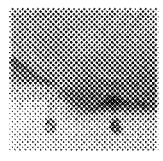

FIG. 33A shows a tumor obtained after injection of MEF RAS-G12V/DNP53 cells expressing the C-terminal tagged Cyclin D1.

Figure 33B:
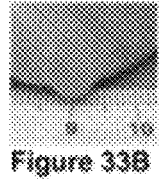

FIG. 33B shows a tumor obtained after injection of MEF RAS-G12V/DNP53 cells expressing C-terminal tagged Cyclin D1, 9 hours after treatment with an anti-tag siRNA.

Figure 33C:
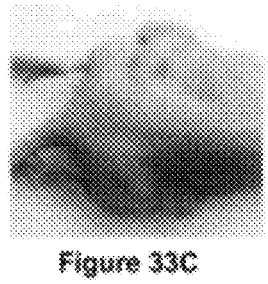

FIG. 33C shows the back of a mouse where one can see, on the left flank, a tumor obtained after injection of MEF RAS-G12V/DNP53 cells expressing the C-terminal tagged Cyclin D1 and on the right flank, a tumor obtained after injection of MEF RAS-G12V/DNP53 cells expressing Cyclin D1.

Figure 33D:
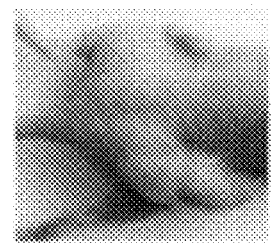

FIG. 33D shows the back of a mouse where one can see, on the left side, a tumor obtained after injection of MEF RAS-G12V/DNP53 cells expressing the C-terminal tagged Cyclin D1 and on the right flank, a tumor obtained after injection of MEF RAS-G12V/DNP53 cells expressing the Cyclin D1, 5 days after treatment with an anti-tag siRNA. The tumor on the left flank has been reduced, while that on the right flank has become larger.

Figure 34:
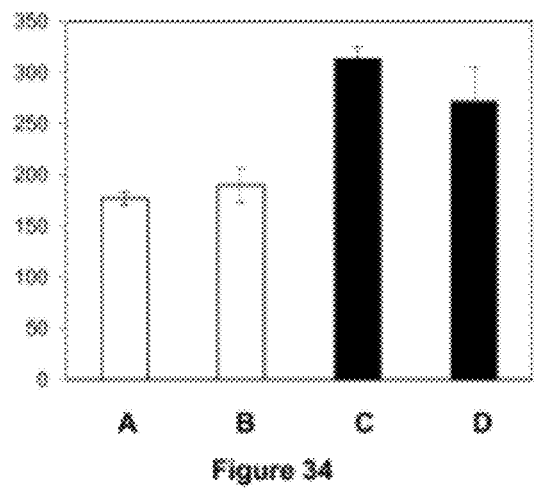

FIG. 34 shows a graph showing the size of the tumors (in mm$^3$) obtained from two independent clones of MEF RAS-G12V/DNP53 cells expressing the N-terminal tagged Cyclin D1 and under the dependency of a nonoptimal Kozak sequence (A and B) or expressing the non-tagged Cyclin D1 under the dependency of the wild Kozak (C and D). The error bars correspond to the standard deviation of 10 tumors.

Figure 35:
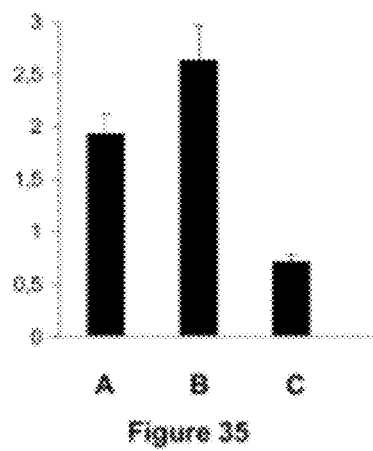

FIG. 35 shows a graph showing the increase in the tumors obtained from MEF CCND1-/- cells transformed with RAS-G12V/DNP53 and expressing the tagged Cyclin D1 under the control of the wild promoter (A) or under the control of the mutated promoter (mutation −7C/G; B and C) for three days after treatment with nonrelevant siRNAs (A and B) or anti-HA (C). The error bars correspond to the standard deviation over 10 tumors.

Figure 36:
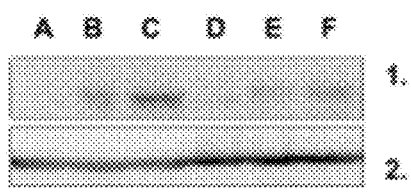

FIG. 36 is a Western blot showing the expression of the human Cyclin D1 (1.) expressed in MEF CCND1-/- (A and D) or MEF CCND1-/- expressing the tagged human Cyclin D1 under the control of the wild promoter (B and E), or under the control of a mutated promoter (mutation −7C/G; C and F). The cells are cultivated in the presence (A to C) or absence (D to F) of serum.

Figure 37:
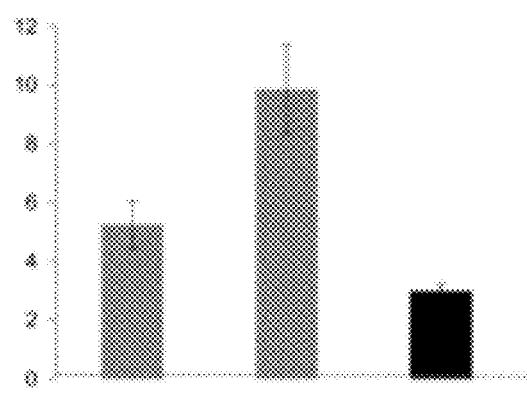

FIG. 37 shows a graph showing the increase in tumors obtained from MEF cells expressing Large T and the RAS-G12V oncogene under the control of an optimal Kozak sequence (B and C) or under the control of a nonoptimal Kozak sequence; A) for three days after treatment with nonrelevant siRNA (A and B) or anti-HA (C). The error bars correspond to the standard deviation over 10 tumors.

EXAMPLES

Example 1

Summary

The inventors have discovered that Cyclin D1 performed a function in differentiated adult tissues protecting against environmental stresses. The inventors found that Cyclin D1 acts directly by interacting with caspase 3 to preserve the integrity of the Poly ADP Ribose Polymerase (PARP) and inhibit programmed cell death. Unfortunately, this function participates in tumor development and increases resistance to chemotherapy independently of the CDK4/CDK6 functions. Cyclin D1 is therefore a cornerstone of tumor development, and the need to decrease it is a key to cancer treatment.

Results

Cyclin D1 is Expressed in the Organs

Figure 1:
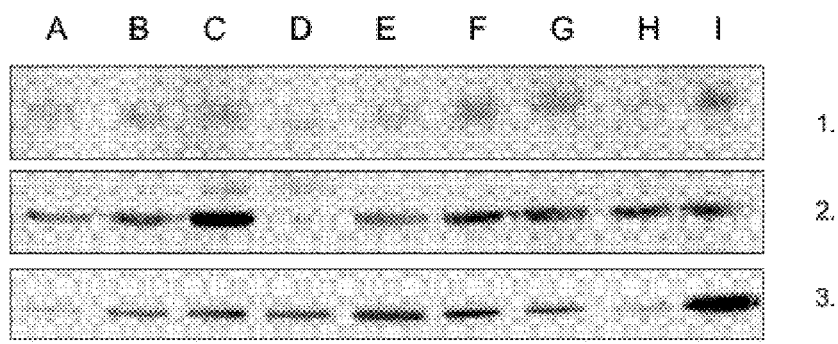

The inventors previously generated FLAG-HA-Cyclin D1 mice, where the FLAG-HA tag is positioned in C-terminal or N-terminal of the protein. These mice develop normally and regulate the tagged protein (whether a C-terminal or N-terminal tag) in the same way as the wild protein, since the promoter has been maintained. Under normal maintenance conditions of the mice, the two types of mouse develop and grow without developing visible pathological signs, unlike animals invalidated for the CCND1 gene. The Cyclin D1 is considered dispensable at the adult age, but although it is difficult to demonstrate, the wild Cyclin D1 is expressed in the adult organs (FIG. 1). However, the C-terminal tagged Cyclin D1 is easily detectable in the adult tissue using the HA tag (FIG. 2 and FIG. 3).

Figure 2:
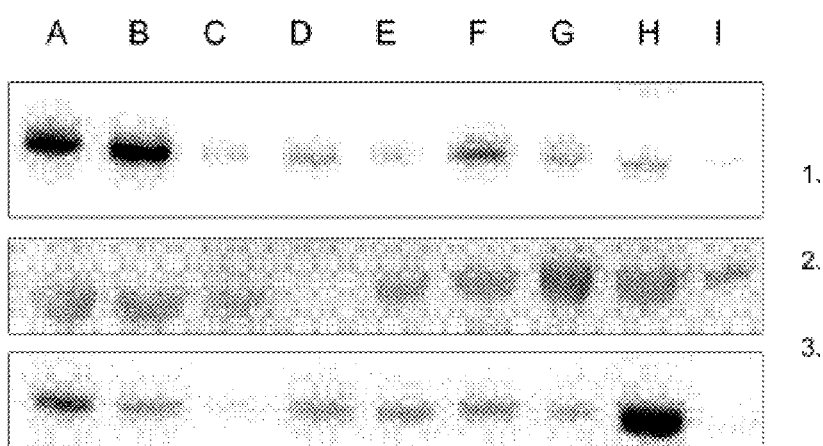
Figure 3:
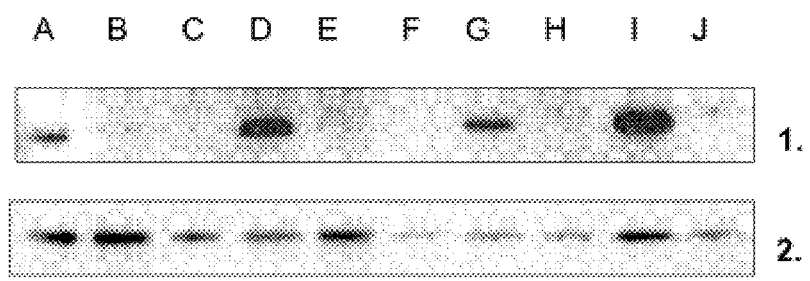
Figure 4:
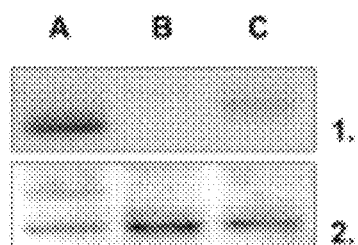
FIG. 4 shows a Western blot showing the expression of the tagged Cyclin D1, revealed by the anti-HA antibody (1.) in the mouse's eye: A: Ctag/+ heterozygotes for the C-terminal tagged Cyclin D1 protein, B: +/+, and C: Ntag/+ heterozygotes for the N-terminal tagged Cyclin D1 protein. The extracts are normalized with tubulin (2.).

Surprisingly, the N-terminal tagged protein is less expressed than the wild protein or the C-terminal tagged protein (FIG. 4 and FIG. 2).

A mutation of the N-terminal tagged Cyclin D1 is found in the Kozak sequence, which results in causing an effective translation defect of the protein. Indeed, the sequences coding the tagged proteins in the N-terminal position are placed under the control of a mutated Kozak sequence 5'-GGCCGCGCCATATGG-3' (SEQ ID NO: 9), while the sequences coding the C-terminal tagged proteins are placed under the control of a wild Kozak sequence 5'-GGC-CGCGCCATGG-3' (SEQ ID NO: 10).

To precisely measure the decrease in the expression of the N-terminal tagged Cyclin D1, relative to the C-terminal tagged Cyclin D1, the inventors have developed a method for detecting the energy transfer by time-resolved Förster resonance (TR-FRET), providing a high detection sensitivity of the tagged proteins. The TR-FRET is based on the transfer of energy from a donor antibody, activated at a certain wavelength, to an acceptor antibody activated by the fluorescence emitted after excitation by the donor antibody. In the lysates of mice expressing a tagged Cyclin D1 protein, TR-FRET is possible between a donor anti-FLAG antibody and an acceptor anti-HA antibody, and vice versa. By using cell or organ lysates, the quantification of the tagged Cyclin D1 protein is precise, even at low levels, and may further be improved by choosing different donor antibody/acceptor antibody pairs (FIGS. 5A and 5B). These results show that the N-terminal tagged protein is 2 to 3 times less expressed than the wild protein or the C-terminal tagged protein in most of the organs (FIG. 6).

The Cyclin D1 Protects Against Stress Induced by Tissue Damage in the Adult Substantia Nigra, the Adult Heart and the Adult Testicles The presence of Cyclin D1 in the adult tissues poses the question of its physiological role outside cell proliferation. The invalidation of the gene coding the Cyclin D1 is associated with retinal hyperplasia and neurological disorders. The genomic analyses and programming analyses in the cells of the retina have shown that the Cyclin D1 was interacting with several biomarkers involved in the etiology of Parkinson's disease.

In fact, the inventors have shown that Cyclin D1 is expressed in the substantia nigra, site where the death of dopaminergic neurons is a characteristic in patients with Parkinson's disease. (FIGS. 7A to 7H). The inventors tested this region of the brain in N-terminal tagged CCND1 homozygous mice or wild mice (CCND1+/+) by using the 6-hydroxy dopamine (6-OHDA), a neurotoxin used to selectively kill the dopaminergic and noradrenergic neurons. 6-OHDA penetrates the neurons using monoamine transporters, and imperils the cell integrity by oxidative stress.

The wild animals survive treatment, while the mice expressing little Cyclin D1 (expressing the N-terminal tagged Cyclin D1) die several days after 6-OHDA treatment due to the death of the dopaminergic neurons (FIG. 9). Another model of dopaminergic neurons tested with methamphetamine leads to an increase in cerebral lesions in animals expressing little Cyclin D1, while the quantity of Cyclin D1 decreases in the substantia nigra (FIG. 8).

These results show the role that Cyclin D1 plays in neurodegenerative disorders related to the age of the substantia nigra, where it participates in maintaining the longevity of the dopaminergic neurons in response to stresses causing cell death.

In order to determine whether the quantity of Cyclin D1 also influences the survival of heart cells, the inventors tested the susceptibility of animals expressing N-terminal tagged Cyclin D1 to pathological apoptosis by using a protocol causing a myocardial infarction. Anesthetized mice were subjected to an in vivo cardiac ischemia, while performing a reversible ligature of the coronary artery. The size of the infarction and the specific fragmentation of the DNA (a signature of apoptosis) are systematically greater in mice expressing N-terminal tagged Cyclin D1 relative to wild mice (FIGS. 10 and 11). These results show the participation of Cyclin D1 in protection from stress-induced apoptosis. Since caspase 3 plays a key role in ischemia-reperfusion-induced apoptosis, it is possible for the Cyclin D1 to inhibit the cascade of activity (death signal) induced by the caspase 3.

The inventors then tested a third organ by subjecting the animals to methoxyacetic acid (MAA). MAA is present in many industrial products, and has been demonstrated to have a harmful effect on male germinal cells expressing Cyclin D1, by causing the cascade of activation induced by the caspase 3 (FIGS. 12A to 12H). After an intraperitoneal injection of MAA, the inventors observed, in the testicles of mice expressing N-terminal tagged Cyclin D1, a massive loss of germinal cell marker (Vasa) and an increase in the cleaved PARP rate, signature of the activation of the caspase 3, relative to the wild mice. The decrease in Cyclin D1 after treatment with MAA indicates that it participates in preventing apoptosis induced by caspase 3 (FIG. 13).

Unlike the tissues previously tested, the inventors have not seen any difference in resistance to treatment with palmitate in the Langerhans islets irrespective of the mice tested. The β cells of the pancreas developed primarily via Cyclin D2, but apparently not via Cyclin D1. The Cyclin D2 could be the dominant Cyclin D in these cells where the Cyclin D1 is weakly detectable (FIGS. 1, 2 and 6).

The in vivo results show an intrinsic function of the Cyclin D1 protein: protection against stress-induced cell death in the organs that express it.

Cyclin D1 Inhibits the Cleavage of the PARP and Apoptosis Independently of the CDK4 Kinase Activity In order clarify the function of protecting against apoptosis of Cyclin D1 independently of the CDK4/RB axis, the inventors tested the impact of Cyclin D1 in cell lines immortalized by the T antigen. The T antigen is known to block both the P53 and RB signaling pathways. In these cells, the levels of N-terminal tagged Cyclin D1 remain lower compared to the control cells (FIG. 14). The inventors did not notice statistical differences between the basal apoptosis of the cells without Cyclin D1 and that of the cells having little Cyclin D1, or the FAS/FASL apoptosis is not effective in these cells.

However, the apoptosis induced by ethanol or actinomycin D, a transcription elongation inhibitor, increases with a low Cyclin D1 level, accompanied by strong cleavage of the PARP (FIG. 15).

The PD0332991, a specific inhibitor of CDK4, or the Q-VD-Oph, a pan-caspase inhibitor, shows that the Cyclin D1 inhibits the apoptosis mediated by caspase 3 independently of CDK4 (FIG. 16).

The Kozak sequence of the Cyclin D1 participants in the resistance to apoptosis

The murine embryonic fibroblast MEF cells not expressing Cyclin D1 have a high cleaved PARP rate in response to ethanol compared to the control cells, cleavage that is reversed by the expression of the Cyclin D1 (FIG. 17).

Taking account of the results with animals expressing a N-terminal tagged Cyclin D1, the inventors noted that the better translation is mediated with the wild Kozak sequence, whereas an insertion of an AT before the initiator ATG (Kozak-) induces stronger cleavage of the PARP in the presence of ethanol (FIG. 18).

In the fibroblasts, the levels of Cyclin D1 decrease over time after stress, while the cleavage of the PARP increases, which results in the apoptosis induced by the ethanol being greater when the quantity of Cyclin D1 is suboptimal (FIG. 19).

In light of the significance of the mouse Kozak sequence to prevent apoptosis, the inventors looked at this region in humans. They found a polymorphism (−7C/G) in the heart of the Kozak sequence of the human Cyclin D1 (FIG. 20). The restoration of the Cyclin D1 in the MEFs not expressing Cyclin D1 shows that protein translation levels are high if the translation is controlled by the human mutant sequence (−7G/C) relative to the translation controlled by the wild sequence (SEQ ID NO: 1). The MEFs expressing Cyclin D1 under the control of the mutated sequence have better protection against cleavage of the PARP (FIG. 21), which correlates with the fact that the apoptosis is more reduced in the cells expressing more Cyclin D1 than those expressing less Cyclin D1 (FIG. 22), and reinforcing the idea that the Cyclin D1 has anti-apoptotic properties.

The Cyclin D1 Inhibits Chemotherapy-Induced Apoptosis

In light of the prevalence of the increase of Cyclin D1 in human pathologies, the inventors evaluated the impact of Cyclin D1 and its invalidation in the survival of cancer cells. CCND1−/−, CCND1Ctag/Ctag, CCND1Ntag/Ntag or CCND1+/+ MEFs were transformed with a P53 negative dominant and a RAS oncogenic mutant (RAS G12V). The null Cyclin D1 cells, or those expressing low or high Cyclin D1 levels, were then treated with 5-fluorouracil (5-FU), an intercalary agent, or actinomycin D, which blocks transcription. The inventors were able to show that the quantity of Cyclin D1 correlates with the decrease in the apoptosis rates, showing that the Cyclin D1 inhibits stress-induced apoptosis in tumor cells also (FIG. 23).

The Cyclin D1 activates CDK4 to favor the tumor progression via MMTV-ErbB2, but the pharmacological inhibition of CDK4 does not appear to affect RAS-mediated apoptosis after treatment with 5-FU (FIGS. 24 and 25). To evaluate the effect of Cyclin D1 on the survival of ErbB2 cells, the inventors generated CCND1++ and CCND1Ntag/Ntag cells from a tumor model of the mammary gland. The inhibition of the tagged Cyclin D1 in the ErbB2 cells increases the apoptosis induced by the 5-FU. The ethanol-induced apoptosis is also increased by the invalidation of the tagged Cyclin D1 in the RAS and ErbB2 lines, but without involving CDK4 inhibition. Consequently, the Cyclin D1 modulates the cell death of the tumor cells independently of CDK 4, but via an activation of the caspases, since the Q-VD-Oph shunts the apoptosis in these experiments (FIGS. 24 and 25).

Compared to the fibroblasts immortalized by the T antigen, the confluence or weaning in serum only slightly affects the level of Cyclin D1 in the RAS or ErbB2 tumor cells. However, in the same way, increased resistance to stress-induced apoptosis in the MMTV-ErbB2 or RAS/P53 cells strongly expressing Cyclin D1 is observed, and appears disconnected from the extracellular myogenic signals. These results show that under harmful conditions, Cyclin D1 inhibits apoptosis induced by the caspase 3 of the tumor cells outside any regulation of the cell cycle.

The Cyclin D1 is Associated with Caspase 3

In the interactomes published on the Cyclin D1, no player in apoptosis has been described. Compared to the abundant partners, such as CDK, the detection by mass spectrometry of transitional interactants of Cyclin D1 is difficult due to their low representativeness. Consequently, the inventors have designed a technique seeking to freeze the interactions, through partial chemical fixing, in order to reveal new partners of the Cyclin D1. By using MMTV-ErbB2 tumor cells fixed to the formaldehyde, the inventors have captured Cyclin D1 and analyzed the interactants by mass spectrometry, and have identified the caspase 3. The inventors verified the Cyclin D1/Caspase 3 interaction, which appeared undetectable by capturing the C-terminal tagged Cyclin D1 from RAS/P53 cells without prior chemical fixing, which can explain why caspase 3 was never found to be associated with Cyclin D1 in the preceding interactomes (FIG. 26).

The caspase 3 is the major effector caspase of apoptosis. The PARP plays a fundamental role in controlling the integrity of the genome by catalyzing the distillation of the genome and is a substrate for the caspase 3. The levels of cleaved PARP increase in RAS or ErbB2 cancer cells after treatment with 5-FU, although limited by the Cyclin D1, which confirms the inhibiting effect of Cyclin D1 on the activation of caspase 3 in the tumor cells (FIG. 27).

The Use of siRNA Shows that Cyclin D1 is the Achilles' Heel of Tumors

In light of the relatively unfavorable environment in which cancers develop, the inventors consider that inhibiting the expression of Cyclin D1 by interference with RNA will affect tumor growth.

The inventors first restored the expression of the Cyclin D1 in MEFs not expressing any, by forcing the expression of a hyperstable Cyclin D1 (T286A mutant), and showed the specific effect of siRNA directed against the tags (FIG. 28). They then transformed the 3T3 wild cells with the T286A mutant, and implanted the cells in nude mice. The anti-HA or anti-FLAG siRNAs show an effect on tumor progression (FIGS. 29 and 30).

Next, by using MEFs expressing C-terminal tagged Cyclin D1, N-terminal tagged Cyclin D1, or expressing wild Cyclin D1, and transformed by RASV12 and negative dominant P53, the inventors showed that the siRNA against the tags rapidly inhibit the tumors except those expressing the wild protein (FIG. 31, FIG. 32 and FIGS. 33A to 33D).

These results show that the Cyclin D1 participates in the development and maintenance of the tumors from these cell lines.

Next, in a cell model derived from MMTV/ErbB2× CCND1Ntag/Ntag or MMTV-ErbB2×CCND+/+ crossing, the innovation of the N-terminal tagged Cyclin D1 by anti-tag siRNAs also induces a tumor regression. Cyclin D1 is therefore a target of first choice against cancer.

The inventors noted that the tumor progression of the RAS-G12V/DNP53 tumors expressing low levels of Cyclin D1 (N-terminal tagged Cyclin D1), due to the presence of a deficient Kozak sequence, progress more slowly compared to tumors expressing wild protein or the C-terminal tagged protein (FIG. 34). To evaluate the oncogenic impact of the mutation of the Kozak sequence, the inventors tested tagged human forms of Cyclin D1 expressed strongly or weakly (FIG. 35). These human proteins are functional and respond to extracellular stimuli (FIG. 36). Interestingly, MEFs transformed by RAS-G12V/DNP53 and not expressing Cyclin D1 do not allow tumor development, and are eliminated from the injection site, confirming that Cyclin D1 is necessary for tumor formation in this model. However, the reintroduction of the human Cyclin D1 protein makes it possible for tumors to develop, dose-dependently, suggesting that the quantity of human Cyclin D1, and de facto the mutation increasing the expression of the protein, is a poor prognosis (FIG. 34). Lastly, the invalidation by siRNA of human Cyclin D1 shows that Cyclin D1 plays a role in maintenance of the tumor (FIG. 34).

The RAS oncogene is also considered a good target to inhibit tumor development. The inventors show that mutations of the Kozak sequence or invalidation by siRNA can interfere with the development of the tumor under the influence of RAS-G12V. In the same logic, the inventors have noted rapid tumor progression of tumors expressing large quantities of RAS (under the control of a Kozak sequence of RAS increasing the expression) compared to the tumors exposing a lower quantity of RAS (under the control of the normal Kozak sequence), and the invalidation by siRNA directed against RAS reduces the tumor (FIG. 37).

Conclusion

The inventors have described an unexpected in vivo role of Cyclin D1 in differentiated organs in response to stress-induced apoptosis. The interaction with caspase 3 and the inhibition of the cleavage of the PARP directly link Cyclin D1 to the control of genomic instability. The inhibition of caspase 3, in response to environmental stress, appears beneficial for healthy adult tissues, but may on the contrary be harmful in tumor cells by creating resistance to chemotherapy. This new function of Cyclin D1 is involved in DNA repair and the induction of genomic instability of oncogenes. This means that independently of the CDK4, the cells use Cyclin D1 to 1—repair the damage to the DNA, 2—inhibit chemotherapy-induced apoptosis, and 3—control genomic instability. The regulation of apoptosis by Cyclin D1 is therefore a new therapeutic angle to be taken into consideration in the context of tumor treatment. However, such treatments targeting Cyclin D1 should be used with caution in order to account for the normal function of Cyclin D1 and healthy tissues.

The other Cyclins in the family have similar anti-apoptotic functions. For example, Cyclin D2 has an effect in pancreas cells, and Cyclin D3 in hematopoietic cells.

Materials and Methods

Mice

The CCND1Ntag/Ntag and CCND1Ctag/Ctag mice were previously described in Bienvenu, F., et al., Nature, 2010. 463(7279): p. 374-8. The C57BL/6J and 129v gene pools were obtained for at least three crossings of descendants with one another. The animals were obtained according to approved procedures (Institut de génomique fonctionnelle [Institute of Functional Genomics]; agreement A 34-513) and approved by the regional ethics committee (agreement CEEA-LR-12070). The mice were raised at the Institut de génomique fonctionnelle under brightness conditions of 12 hours per day, at a stable temperature of 22±1° C., under controlled humidity conditions (55±10%).

Genotyping

The genotyping is described in Bienvenu, F., et al., Nature, 2010. 463(7279): p. 374-8.

Murine Embryonic Fibroblast (MEF) Cells

The CCND1−/− MEFs were graciously donated by Piotr Sicinski.
The MEFs were cultivated in the Dulbecco medium (DMEM; 41966-029, Gibco) completed with 10% beef serum (Life technology) and 1000 U/mL of penicillin-streptomycin (P/S) (Gibco). All of the cell lines were incubated in an incubator at 37° C. in an atmosphere comprising 5% $CO_2$, and maintained under sub-confluent conditions. Irrespective of the conditions, the MEFs were immortalized with the T antigen or transformed with a combination of RasV12 and a negative dominant p53.

Cohorts of Mice

The CCND1Ntag/Ntag and CCND1Catg/Ctag mice were provided by P. Sicinski.
The animals were crossed with one another using C57BL/6J or 129Sv females from Charles River. Then, cohorts of C57BL/6J homozygotes were obtained from crossing C57BL/6J CCND1Ntag/+ males and C57BL/6J CCND1Ntag/+ females, or from C57BL/6J CCND1Ctag/+ males and C57BL/6J CCND1Ctag/+ females. Cohorts of 129SV homozygotes were obtained from crossing 129SV CCND1Ntag/+ males and 129SV CCND1Ntag/+ females, or from 129SV CCND1Ctag/+ males and 129SV CCND1Ctag/+ females. If no gene pool is specified, it involves a mixture of the two gene pools (1:1).

Treatment of the Mice

Before the experiments, the mice were manipulated as previously described in Ares-Santos, S., et al., Neuropsychopharmacology. 2014, 39(5): p. 1066-80.
The methamphetamine was dissolved in a saline solution at 0.9% (weight/volume) sodium chloride, and injected at a rate of 10 mL/Kg. Several doses of methamphetamine (3 doses of 5 mg/kg at 3 h intervals) were injected intraperitoneally, the first dose being injected at noon. The control mice were treated with the saline solution alone. The mice were sacrificed 24 hours after treatment, for the postmortem analyses.
The methoxyacetic acid 98% (194557-50G, Sigma-Aldrich) was dissolved in a saline solution at 0.9% (weight/volume) sodium chloride, and a simple intraperitoneal injection (150 mg/kg) was injected in the males. The control mice were treated with the saline solution alone. The mice were sacrificed 14 hours after treatment, for the postmortem analyses.

6-OHDA Lesions

The mice were anesthetized with a mixture of ketamine (Imalgene 500, 50 mg/mL, Merial), 0.9% saline solution (weight/vol) and xylazine (Rompun 2%, 20 g/ml, Bayer) (2:2:1, i.p., 0.1 mL/30 g) and mounted on a stereotaxic apparatus. The 6-OHDA-HCl (Sigma) was dissolved in 0.02% ascorbic acid in a saline solution at a concentration of 3 μg of 6-OHDA/μL. Each mouse received two unilateral injections of 6-OHDA (2 μL/injection) in the right dorsal striatum, according to the following coordinates (in mm): anteroposterior +1, mediolateral −2.1, dorsal ventral −3.1 and anteroposterior +0.3, mediolateral −2.3, and dorsal ventral −3.1. The animals are then released and received a daily injection of glucose solution (50 mg/mL, subcutaneous).

Preparation of the Tissues for Immunofluorescence

The mice were anesthetized with phenobarbital (500 mg/kg, i.p., Sanofi-Aventis, France), and perfused through the trans-cardiac route with 4% paraformaldehyde (weight/volume) in 0.1M of saline solution (PBS, pH 7.5). The brains and testicles were post-fixed in the same solution and stored at 4° C.

Immunofluorescence of the Brains

Cuts of 30 μm were obtained with a vibratome (Leica, France) and stored at −20° C. in a solution comprising 30% (vol/vol) ethylene glycol, 30% (vol/vol) glycerol, and 0.1 M sodium phosphate buffer, until the immunofluorescences are done. The cuts were treated as follows: the cuts are rinsed in Tris saline buffer (TBS: 0.25 M Tris and 0.5 M NaCl, pH 7.5), incubated for 5 min. in TBS containing 3% $H_2O_2$ and 10% methanol (vol/vol), and next rinsed three times for 10 min. in TBS. After 15 min. of incubation in 0.2% (vol/vol) Triton X-100 in TBS, the cuts are rinsed again three times in TBS. The cuts are then activated for 1 h in a solution of BSA 3% in TBS. Lastly, the cuts are incubated overnight or for 48 hours at 4° C. with the primary antibodies: mouse anti-tyrosine hydroxylase (TH) (1:1000, Millipore), rat anti-dopamine transporter (DAT) (1:1000, Millipore). After integration with the primary antibodies, the cuts are rinsed three times for 10 min. in TBS and incubated for 45 min. with goat or donkey antibodies coupled with Cy3- or Cy5 (1:400, Jackson Lab). The cuts are then rinsed for 10 minutes twice in TBS and twice in TB (0.25 M Tris) before being mounted in 1,4-diazabicyclo-[2.2.2]-octane (DABCO, Sigma-Aldrich) or DPX (Sigma-Aldrich).

Immunofluorescence of the Brains

Cuts of three micrometers were obtained with a vibratome (Leica, France) and stored at −20° C. in a solution containing 30% (vol/vol) ethylene glycol, 30% (vol/vol) glycerol and 0.1M phosphate buffer until their use for immunofluorescence. The cuts were treated as follows: Day 1: The cuts were rinsed with a TBS saline solution (TBS; 0.25 M Tris and 0.5 M NaCl, pH=7.5). Then, the cuts were incubated at 80° C. in a citrate buffer with pH 6 containing 0.02% Tween, for 30 min., and rinsed three times with the TBS solution. After activation for 30 min. in a TBS buffer containing 0.3% Triton X-100, the cuts were rinsed three times in TBS and blocked for 1 h in TBS comprising 3% bovine serum albumin (BSA) or 3% donkey serum. The cuts were incubated in a solution of 1% BSA, 0.15% Triton X-100 in TBS for 12 to 72 hours with different antibodies against the mouse tyrosine hydroxylase (TH) (1:1000, Millipore) or against the HA tag (1:500, 715500, Life technologies). Day 2: The cuts were rinsed three times for 10 min. in TBS and the secondary donkey, anti-rabbit antibodies marked with Alexa Fluor® 594 (1:500, A-21207 Molecular Probes) or anti-mouse donkey marked with Alexa Fluor® 488 were incubated for 45 min. The cores were marked with 4',6'-diamidino-2-phenylindole (DAPI; 1:5000). The cuts were rinsed twice for 10 min. with TBS and twice with a Tris buffer (0.25 M Tris, pH=7.5), before being mounted on a slide with FluorSave™ (345 79, Merck Millipore).

The immunofluorescence tests of the testicles were described in Malki, S., et al. EMBO J, 2005. 24(10): p. 1798-809.

Briefly, the testicles were included in paraffin and cuts of 5 μm the core were done. After rehydration, the primary anti-TRA98 antibody (1:500 provided by B. Boizet) or HA (715500, Invitrogen) was used, and the secondary antibodies as mentioned above were used. The confocal cuts were analyzed by microscopy (LSM780, or Axiolmager Z1-Dr, Zeiss).

Surgical Preparations for Myocardial Reperfusion Ischemia

The ischemias and reperfusion of the myocardium were done on CCND1Ntag/Ntag mice and, as control, the CCND1+/+ mice. The mice were anesthetized by intramuscular injection of a mixture of ketamine (50 mg/kg; Imalgene® 500; Merial, France), xylazine (10 mg/kg; Rompun® 2%; Bayer, France) and chlorpromazine (1.25 mg/kg; Largactil® 5 mg/ml; Sanofi-Aventis, France) and ventilated by tracheal incubation with a respirator for rodents by Harvard (current volume 7.2 μL/g of body weight; 200 respiration per min.). The temperature was kept between 36.8 and 37° C. After a second injection of ketamine (50 mg/kg) and xylazine (10 mg/kg), the chest is opened by a tracheotomy done on the left and the left coronary artery is ligated by prosthetic occlusion element pause. After 5 min. of thermal stabilization, all of the animals are left for 30 min. in ischemia. The reperfusion is obtained by removing the occlusive device from the artery. At the end of the reperfusion, the coronary artery is re-ligated and 0.10 mL of phthalocyanine blue is injected into the ventricular cavity to perfuse the portions of the myocardium that are not ischemic. The hearts are removed, dissected (the atrium and the right ventricle are removed) and studied to measure the infarction and the fragmentation of the DNA.

Measurement of the Size of the Infarction

The hearts are dissected and the left ventricles are cut transversely into 1 mm cuts and intubated in a solution of 1% TTC (2,3,5-triphenyltetrazolium chloride; Sigma-Aldrich) for 15 min. at 37° C. After fixing in a phosphate saline buffer comprising 4% paraformaldehyde (4% PFA-PBS), the cuts are weighed, and each face is photographed with an Olympus camera. The ischemia risk area (area not treated in blue) and the infarction area (not marked by the TTC) are measured by planimetry by using Image J (Scion corp., Frederick, Md.). The size of the infarction is expressed as a percentage of the ischemic risk area.

Measurement of the Fragmentation of the DNA After Myocardial Infarction

The specific fragmentation of the DNA is quantified in transmutal samples of ischemic or non-ischemic areas with the enzyme-linked immunosorbent assay kit (Roche Diagnostics) used to measure the quantity of DNA linked to the nucleosome. Transmural samples of 30 mg of the non-ischemic area of the left ventricle and the ischemic areas are removed from the mice. The tissues are dilacerated in 400 μL of buffer provided in the kit. The obtained homogenates are centrifugated at 13000 g for 10 min. The supernatant is used as antigen source for an ELISA test. The incubation buffer and a DNA/Histones complex are used as negative controls. Two double absorbency values (405 nm/490 nm) were obtained to take an average; and the background noise was subtracted from each of these averages. To normalize the DNA fragmentation, the soluble nucleosomes derived from the ischemic and non-ischemic regions were tested.

Re-Nutrition Test

The blood glucose levels were measured using a One-Touch Ultra glucometer (LifeScan, Issy les Moulineaux, France) after one night of weaning and three hours of re-nutrition.

Caspase Activity in the Pancreatic Islets

The caspase activity was measured in mouse islets using the Caspase-Glo 3/7 assay kit (Promega) according to the manufacturer's recommendations. Briefly, 48 hours after treatment with 0.5 mM of palmitate, groups of 6 islets are transferred into plates with 96 wells in 100 μL of culture medium. The islets are then lysed with 100 μL of Caspase-Glo 3/7 reagent and incubated at ambient temperature for 30 min. The luciferase activity is measured with an Infinite M200 Tecan microplate reader.

In Vivo Injection of the siRNA and Measurement of the Size of the Tumors

The siRNA were dissolved in water without nucleases and stored at −20° C. before use. A solution of Aonys® (MedesisPharma) was prepared simultaneously. According to the manufacturer's instructions, the Aonys®/siRNA mixture was obtained by mixing using a vortex. The mixture is left at ambient temperature before use.

The Aonys®/siRNA mixture (1 mg/mL) was injected rectally using a micropipette at a constant volume of 20 μL per dose.

The treatment of the tumors by the siRNA was done twice per day (morning and afternoon) every day. The size of the tumors was measured using the following formula: $L \times W^2/2$, where L is the length and W is the width of the tumor mass.

Xenografts

3T3 cells transformed by: $2 \cdot 10^6$ cells per implantation.
MEFs transformed by RAS-G12V/DNP53: $0.5 \cdot 10^6$ cells per implantation.
The MEFs immortalized by the T antigen: $0.5 \cdot 10^6$ cells per implantation.
Each cell type is reacted in 150 μL of RPMI 1640 and injected into the athymic mouse flank at 6 weeks subcutaneously.

Cells

The MEFs are cultivated in DMEM comprising 10% fetal beef serum, and 1000 U of Penicillin-Streptomycin. The primary cells derived from the tumors are kept in DMEM comprising 5% serum and 1000 U of Penicillin-Streptomycin. All of the cells are cultivated at 37° C. in the presence of 5% $CO_2$. When so specified, the serum is removed for 36 hours.

Primary Cultures of MMTV-ErbB2 Mammary Tumors

The tumors are withdrawn from animals and washed in PBS 1× and cut. The tumor pieces are reacted in a mixture of trypsin (1.25 mg/mL), type I collagenase (1000 units/mL) and Penicillin-Streptomycin (1000 units/mL) in the DMEM/F-12 medium at 37° C. for 20 min. under agitation. Then, the dissolved tissues are resuspended in an inhibitor cocktail of trypsin (0.5 mg/mL) and DNAse I (370 units/mL).

The epithelial and fibroblast cells are separated by sedimentation at 1000 g for 10 min. and reacted in medium, then sown in the DMEM containing 5% serum and the antibiotics and left for 24 to 48 h in culture. The cells are kept at a sub-confluent stage and the expression of the MMTV-ErbB2 transgene is measured by RT-PCR.

RNA

The RNAs are extracted with Trizol (Invitrogen) according to the manufacturer's instructions. 1 µg of RNA total is used for the reverse transcription in the presence of 200 U of reverse transcriptase of M-MLV (Invitrogen) in the presence of 2.5 µM of random hexamers, 0.5 mM of dNTP, 10 mM of DTT and 40 U of RNAse inhibitor (Invitrogen).

The reference genes used are the following:

Western Blot and Immunoprecipitations

The antibodies used are the following: anti-HA (HA.11 Clone 16B12, Eurogentec or Anti-HA EPITOPE TAG-600-401-384, Tebu-bio or Hemagglutinin (HA) Rabbit Polyclonal Antibody, Life Technologies), anti-Cyclin D1 (sc-450, Santa Cruz or MS-210-PABX (AB1), Fisher Scientific or RB-010-PABX (AB3), Fisher scientific), anti-RB total (sc-74562, Santa Cruz), anti-Phospho-RB (Ser780) (9307, Cell signaling), anti-Actin (ab6276, Abcam), anti-Tubulin (T9026, Sigma-Aldrich), anti-Ras (BD610002, BD Biosciences), anti-FLAG (F7425, Sigma-Aldrich), anti-cleaved PARP (ab32064, Abcam), anti-VASA (ab13840, Abcam), anti-Thyrosine Hydroxylase (MAB318, Merck Millipore). The secondary antibodies used are coupled with peroxidase (signaling), and the detection of the complexes is done using the enhanced chemiluminescence detection kit (Millipore).

Constructions

All of the Cyclin D1 or RAS constructions are inserted between the BamH1-EcoR1 sites of the pBABE-Puro retroviral vectors provided by P. Sicinski or MSCV provided by O. Ayrault. The plasmid decoding the T antigen was provided by L. Fajas, the plasmid decoding RasV12/p53 negative dominant was provided by L. LeCam.

All of the retroviral constructions were manipulated according to the safety measures approved by the Institut de Génomique fonctionnelle.

The human Cyclin D1 complementary DNA (cDNA) was obtained by RT-PCR from skin fibroblast transmitted by Jean-Marc Lemaitre.

Mutagenesis

All of the mutageneses were done using the GeneArt® Site-Directed Mutagenesis System kit (LifeTechnologies) according to the manufacturer's recommendations. The oligonucleotides used are the following:

| Gene | SeqRef | Forward | Clockwise sequence |
|---|---|---|---|
| Aldo3 | NM_009657 | mAldo3-F | CGGCACTGGCCATATTGG (SEQ ID NO: 13) |
| B2µg | NM + 009735 | B2m-F | TATGCTATCCAGAAAACCCCTCAA (SEQ ID NO: 14) |
| GAPDH | NM_008084 | Gapdh-F | GGAGCGAGACCCCACTAACA (SEQ ID NO: 15) |
| Gus | NM_010368 | Gus2-F | GATTCAGATATCCGAGGGAAAGG (SEQ ID NO: 16) |
| Hprt | NM_013556 | Hprt2-F | GCAGTACAGCCCCAAAATGG (SEQ ID NO: 17) |
| Mrpl32 | NM_029271 | Mrpl32-F | AGGTGCTGGGAGCTGCTACA (SEQ ID NO: 18) |
| Tbp | NM_013684 | Tbp2a-F | ATCGAGTCCGGTAGCCGGTG (SEQ ID NO: 19) |
| Tubulin | NM_023716 | Tubb2b-F | CTTAGTGAACTTCTGTTGTTGTCCTCCAGCA (SEQ ID NO; 30) |
| MCyclin D1 | NM_007631 | CCND1-F | AGGAGCAGAAGTGCGAAGAG (SEQ ID NO: 21) |
| hCyclin D1 | NM_053056 | hCCND1-F | GGCGGAGGAGAACAAACAGA (SEQ ID NO: 22) |

| Clockwise oligo-nucleotides | Sequence |
| --- | --- |
| Mutag-mCCND1-T286A- | GGTCTGGCCTGCGCGCCCACCGACGTG (SEQ ID NO: 23) |
| Flag-hKoz-SNP7-hCD1- | GACGATGACAAGGGAAGAGCGCCAGCCATGGAACACCAGCT (SEQ ID NO: 25) |
| hKOZ-snp-hCD1- | gGGATCCggaagagcGccagccATGGAACAC (SEQ ID NO: 27) |
| mKoz-mCCND1- | CAGTGTGGTGGTACGGCGGCCGCGCCatgGAACACCAGCTCCT (SEQ ID NO: 29) |
| mKoz-Flag-HA-mCCND1- | CCAGTGTGGTGGTACGGCGGCCGCGCCatggactacaaggacga (SEQ ID NO: 31) |
| mKoz-AT-Flag-HA-mCCND1- | CCAGTGTGGTGGTACGGCGGCCGCGCCATatggactacaaggacga (SEQ ID NO: 33) |
| Counterclockwise oligo-nucleotides | Sequence |
| Mutag-mCCND1-T286A- | CACGTCGGTGGGCGCGCAGGCCAGACC (SEQ ID NO: 24) |
| Flag-hKoz-SNP7-hCD1- | AGCTGGTGTTCCATGGCTGGCGCTCTTCCCTTGTCATCGTC (SEQ ID NO: 26) |
| hKOZ-SNP-HCD1 | GTGTTCCATggctggCgctcttccGGATCCc (SEQ ID NO: 28) |
| mKoz-m CCND1- | AGGAGCTGGTGTTCcatGGCGCGGCCGCCGTACCACCACACTG (SEQ ID NO: 30) |
| mKoz-Flag-HA-mCCND1- | tcgtccttgtagtccatGGCGCGGCCGCCGTACCACCACACTGG (SEQ ID NO: 32) |
| mKoz-AT-Flag-HA-mCCND1- | tcgtccttgtagtccatATGGCGCGGCCGCCGTACCACCACACTGG (SEQ ID NO: 34) |

Generation of Stable Cell Lines

The cells obtained by retroviral infection were described in Bienvenu et al., Nature, 2010. 463(7279): p. 374-8. Briefly, the day before the infection, the Plat-E cells are sown in 10 cm boxes at 50% confluence in DMEM (Gibco) supplemented with fetal bovine serum.

The murine ecotropic retroviruses were produced by transfection with jetPEI of Plat-E cells with 3 µg of pBabe-puro or MSCV-puro vectors, or with a vector not carrying a resistance gene. Forty-eight hours after the transfection, the viral supernatant was withdrawn, filtered (0.45 µm) supplemented by polybrene (H9268, Sigma) and used to infect the receiving cells and proliferation. Seventy-two hours after the infection, the receiving cell medium was replaced and the cells were left in culture for several days in the presence of 2 µg/mL of puromycin or 130 mg/mL of hygromycin, until death of the control cells (which do not express the resistance gene).

Transfection of the siRNAs

The siRNAs were administered to the cells with Lipfectamine® RNAiMAX Transfection Reagent (Life Technologies) according to the manufacturer's instructions. The cells to be transfected were sown at 9:00 in the morning, and transfected at 6:00 in the evening the same day. The following day at 9:00 in the morning, the cells were harvested for biochemical analyses.

TR-FRET

The mouse organs were washed with PBS 1× at 37° C. and lysed in HTRF buffer (Tris 10 mM, EDTA 1 mM, 0.05% NP-40) using a cell homogenizer. After centrifugation at 16000 g for 5 min., the samples were normalized by adjusting the total quantity of DNA (nanodrop, Thermo Scientific) at 500 ng/mL.

Owing to a Bradford quantification, the total content of proteins was verified to perform equivalence between similar organs or the samples to be tested (for example, CCND1+/+ kidneys and CCND1+/− kidneys). Samples deleted for the two alleles of the Cyclin D1 were tested as negative controls and evaluation of the background noise (control 1). Furthermore, samples included with the donor antibody alone were tested in parallel (control 2). The comparison of the two controls for each measurement yields identical background noise results.

The detection of the Cyclin D1 by HTRF (tagged or not) was done with donor and acceptor antibodies according to the manufacturer's instructions (Cisbio—0.4 nM for the donor except for the SC450 antibody (0.2 nM) and 6 nM as acceptor) in the HTRF signal linear range (in the linearity window of the antibodies), in order to avoid saturation of the signal (hook effect) and an overly weak signal close to the background noise. The donor antibodies are marked with terbium cryptate (Tb), and the acceptor antibodies are marked with fluorophore XL665 or d2.

The antibodies used are the following:
Donor antibodies:
HA-Tb, 610HATAB, Cisbio
Flag-Tb, 61FG2TLB, Cisbio
HA-XL, 610HAXLB, Cisbio
AB3-Tb 64CUSTAYE, Cisbio (custom marking of the RB-010-PABX antibody (AB3), Fisher Scientific)
AB1-Tb 64CUSTAYE, Cisbio (custom marking of the MS-210-PABX antibody (AB1), Fisher Scientific)
SC-450-Tb 64CUSTAZE, Cisbio (custom marking of the SC-450 antibody, Santa Cruz)
Acceptor antibodies:
Flag-XL, 61FG2XLB, Cisbio
AB3-d2 64CUSDAZE, Cisbio (custom marking of the RB-010-PABX antibody (AB3), Fisher Scientific)
AB1-d2 64CUSDAZE, Cisbio (custom marking of the MS-210-PABX antibody (AB1), Fisher Scientific)
SC-450-d2 64CUSDAZEW, Cisbio (custom marking of the SC-450 antibody, Santa Cruz).

For the HTRF measurements, the mixture of the antibodies is adjusted to a volume of 5 µL in PBS 1×, and these 5 µL are adjusted to 5 µm of sample to be tested, in a black plate with 384 wells by Greiner. After agitation and centrifugation, the samples are regulated at 4° C. all night sheltered from light (or 1 h at ambient temperature (from 19 to 25° C.)).

The following morning, the experiment is done using a PHERAstar FS microplate reader (BMG Labtech): after excitation with a 337 nm laser (40 flashes per well), the fluorescence emissions are measured at the same time at 620 nm (emission of the terbium cryptate) and 665 nm (emission of XL665 and d2). The emitted fluorescences are collected for 400 µs (microseconds) after a lag time of 60 ms following the flashes, in order to remove the background noise coming from the medium from the measured signal.

The intensity of TR-FRET is calculated as follows:

$$TR\text{-}FRET=\{(\text{ratio } 600\ 625/620) \text{ sample}\}\times 10^4-\{(\text{ratio } 665/620) \text{ noise}\}\times 10^4$$

The background noise corresponds to the cells marked with the donor antibody alone, or a sample not expressing the target protein. For each measurement, the average of several experiments was used. The data from the figures correspond to the average of several independent experiments +/− standard deviation, unless otherwise indicated.

Measurement of Cell Death

Cell death is induced by exposure to actinomycin D A9415, Sigma, for 6 h, 5-Fluoro uracil (Fluorouracil Winthrop, Sanofi-Aventis) for 24 h, or ethanol (20821.330, VWR) for 6 h and inhibited by exposure to Q-VD-Oph (SML0063, Sigma).

The cells are washed twice in PBS 1×, unstuck with trypsin and reacted in a marking buffer (10 mM of Hepes pH=7.4, sodium chloride 150 mM, KCl 5 mM, $MgCl_2$ 1 mM, $CaCl_2$ 1.8 mM). Then the cells were marked with fluorescein V-fluorescein isothiocyanate (BD Biosciences) according to the manufacturer's instructions in 0.5 µg/mL of propidium iodide (PI; Sigma-Aldrich P-4170). After 15 min. of incubation in the dark, the cells are analyzed by flux cytometry. The living cells are Annexin V and PI double negatives and the apoptotic cells are positive for Annexin V and negative for PI.

Detection of Cell Death by Immunology

The quantification of the cell death in the MEFs is done by using the Cell Death Detection ELISAPLUS kit (11920685001, Roche) according to the manufacturer's instructions. The values obtained in arbitrary units are calculated using the formula: arbitrary unit =Absorbance (405 nm) of the sample (marking/dead cells)/Absorbance (405 nm) of the corresponding negative control. The data correspond to the average of three independent experiments±the standard deviation. The statistical data are done by a student t-test. The values <0.05 are considered to be statistically significant.

Statistical Analyses

The averages of two groups were compared by using a bilateral Student t-test.

Caspase-3 Peptides Identified by Mass Spectrometry

SGTDVDAANLR (SEQ ID NO: 11) (position: 65-75), two MS/MS spectrums
SVDSGIYLDSSYK (SEQ ID NO: 12) (position: 26-38), one MS/MS spectrum Example 2

Experimental Protocol to Test the Impact of a Mutation of the Kozak Sequence on the Expression of a Gene 1—the Kozak Sequence of Interest is Merged with the Ntag-CycD1 Reporter Gene by Cloning:
  Clockwise and counterclockwise oligonucleotides made up of
  a—the cohesive sequence at the restriction site of the enzyme Bam H1, followed by
  b—an advantageous restriction site for the screening described below, for example EcoR1, followed by
  c—the Kozak sequence of interest (−9 to +3 around the ATG codon initiating the translation) in its wild form or in its mutated form, followed by
  c—the cohesive sequence at the restriction site of the Xho1 enzyme, are designed, then assembled by base matching after heating to 90° C. for 3 minutes followed by slow cooling to 4° C.
  The MSCV-Ntag-CycD1 retroviral vector, expressing
  a—a eukaryote selection gene, such as a fluorescent reporter gene for sorting by flux cytometry, or a eukaryote resistance gene, for example to puromycin, and
  b—the Cyclin D1 reporter gene merged with the N-terminal FLAG and HA peptide sequences of the protein,
  is digested by the BamH1 and Xho1 enzymes in order to open it for insertion of the oligonucleotide described above, such that the Kozak sequence will allow the initiation of the translation of the reporter gene in phase with the ATG initiation codon of the translation.
  A ligation reaction allowing the insertion of the oligonucleotide into the MSCV-Ntag-CycD1 vector by reconstitution of the BamH1 and Xho1 sites, is followed by a step for transforming thermo-competent bacteria for screenings of the bacterial clones having inserted the oligo into the vector by acquisition of the resistance to the ampicillin antibiotic whose gene is present in the original MSCV-Ntag-CycD1 vector
  After growth, the amplification of ampicillin-resistant bacterial clones, a plasmid extraction is done for each of these clones, for example using the Qiagen kit (QIAprep Spin Miniprep Kit, Qiagen) and the purification product is digested by the EcoR1 enzyme (or EcoR1 plus the enzyme recognizing the new advantageous restriction site included in the oligonucleotide) in order to identify a new DNA band corresponding to the proper integration of the oligo into the vector.

The vector of interest thus created is then amplified, then purified for transfection in Phoenix cells allowing the generation of vector viruses of the desired construction.

The viruses thus produced are used to generate stable lines resistant to puromycin that will make it possible to measure the expression of the Ntag-CycD1 reporter gene in a wild Kozak sequence situation relative to the mutated sequence to be analyzed.

A quantification step by qPCR of the messenger RNA of the Ntag-CycD1 reporter gene makes it possible to ensure an equivalent level of transcription between the two lines to be compared.

The lines selected with puromycin thus produced are sown with equivalent confluence for semi-quantification of the expression of the Ntag-CycD1 reporter using an immunoblot, Tandem-HTRF or any other protein quantification method by specific antibody of Ntag-CycD1, after lysis of the cells, then protein extraction.

A load control makes it possible to ensure the proper comparison of the equivalent total quantity of proteins between the two samples (for example, a protein of a housekeeping gene such as GAPDH, Tubulin or Actin).

Different expression levels of the reporter gene attests to the impact of the mutation of the Kozak sequence on the translation level of the gene downstream from the quantity of equivalent messenger RNA attested to by the qPCR measurement done above 2—the Kozak Sequence of Interest is Merged with the Ntag-CycD1 by Directed Mutagenesis:

A directed mutagenesis reaction is done on the Kozak sequence (−9 to +3 around the ATG codon initiating the translation) of the MSCV-Ndel-Ntag-CycD1 vector allowing the expression of the Ntag-CycD1 reporter, using a mutagenesis kit, such as the GeneArt® Site-Directed Mutagenesis System kit from Thermo Fisher (Catalog number: A13282), and owing to the use of oligonucleotides comprising the Kozak sequence of interest to be tested framed by 15 upstream nucleotides corresponding to the 15 upstream nucleotides of the Kozak sequence initiating the translation of the Ntag-CycD1 reporter and 15 downstream nucleotides corresponding to the 15 downstream nucleotides of this same sequence initiating the Ntag-CycD1 translation. The number of 15 nucleotides is provided for information and may vary by several nucleotides.

This mutagenesis step is followed by a step for transforming thermo-competent bacteria for screenings of bacterial clones having acquired resistance to the ampicillin antibiotic whose gene is present in the original MSCV-Ntag-CycD1 vector.

After growth, then amplification of the ampicillin-resistant bacterial clones, a plasmid extraction is done for each of these clones, for example using the Qiagen kit (QIAprep Spin Miniprep Kit, Qiagen) and the purification product is digested by the Eco-R1 and Ndel enzyme in order to identify the clones having lost the Ndel site after mutagenesis of the Kozak sequence of the MSCV-Ntag-CycD1 vector. A confirmation of this mutagenesis is next done by sequencing of positive clones to ensure the absence of untimely mutations in the sequence coding for the Ntag-CycD1 reporter gene.

The vector of interest thus created is then amplified, then purified for transfection in Phoenix cells allowing the generation of vector viruses of the desired constructions.

The viruses thus produced are used to generate stable lines resistant to puromycin that will make it possible to measure the expression of the Ntag-CycD1 reporter gene in a wild Kozak sequence situation relative to the mutated sequence to be analyzed.

A quantification step by qPCR of the messenger RNA of the Ntag-CycD1 reporter gene makes it possible to ensure an equivalent level of transcription between the two lines to be compared.

The selected lines with puromycin thus produced are sown with equivalent confluence for semi-quantification of the expression of the Ntag-CycD1 reporter using an immunoblot, by Tandem-HTRF or any other protein qualification method by specific antibody of Ntag-CycD1, after lysis of the cells, then protein extraction.

A load control makes it possible to ensure the proper comparison of the equivalent total quantity of proteins between the two samples (for example, a protein of a housekeeping gene such as GAPDH, Tubulin or Actin)

Different expression levels of the reporter gene attests to the impact of the mutation of the Kozak sequence on the level of translation of the gene downstream from the quantity of equivalent messenger RNA attested to by the qPCR measurement done above.

3—the Kozak Sequence of Interest is Amplified by PCR with the Complementary DNA of the Downstream Gene that it Controls:

The complementary DNA, of cells expressing the gene for which a mutation of the Kozak sequence must be analyzed, is obtained by total RNA extraction, for example using the Qiagen kit (RNeasy Mini Kit, Qiagen), followed by a traditional Reverse Transcription reaction A PCR reaction is done with this complementary DNA as matrix and with a pair of nucleotides designed such that it will allow the application of the gene of interest preceded by a—any several nucleotides, followed by b—the BamH1 restriction site, followed by c—an advantageous restriction site for the screening described below, for example Nde1, followed by d—the Kozak sequence of interest (−9 to +3 around the ATG codon initiating the translation) in its wild form or in its mutated form; followed by the restriction site for the EcoR1 enzyme, then any several nucleotides.

This PCR product is next digested by the BamH1 and EcoR1 enzymes, then purified in order to allow it to be inserted into the following MSCV vector. It is understood that if the BamH1 and EcoR1 restriction sites are present in the complementary DNA of the gene of interest, other pairs of enzymes will need to be selected for an insertion into a retroviral vector appropriate for these sites.

The MSCV-Ntag-CycD1 vector, expressing a—a eukaryote selection gene, such as a fluorescent reporter gene for flux cytometry sorting, or a eukaryote resistance gene, for example to puromycin, and b—the Cyclin D1 reporter gene merged with the N-terminal FLAG and HA peptide sequences of the protein, is digested by the BamH1 and EcoR1 enzymes in order to remove the Ntag-CycD1 reporter gene for insertion of the purified PCR product described above.

A ligation reaction allowing the insertion of this PCR product into the empty MSCV vector by reconstitution of the BamH1 and EcoR1 sites, is followed by a step for transforming thermos-competent bacteria for screening of the bacterial clones having inserted the oligo in the vector by acquisition of the resistance to the ampicillin antibiotic, whose gene is present in the original MSCV-Ntag-CycD1 vector After growth, the amplification of ampicillin-resistant bacterial clones, a plasmid extraction is done for each of these clones, for example using the Qiagen kit (QIAprep Spin Miniprep Kit, Qiagen), and the purification product is digested by the EcoR1 and Nde1 enzymes or any other enzyme recognizing the new advantageous restriction site included in the PCR product in order to identify a new DNA band corresponding to the proper integration of the PCR product in the vector.

The vector of interest thus created is then amplified, then purified for transfection in Phoenix cells allowing the generation of vector viruses of the desired construction.

The viruses thus produced are used to generate stable lines resistant to puromycin that will make it possible to measure the expression of the gene of interest in a wild Kozak sequence situation relative to the mutated sequence to be analyzed.

A quantification step by qPCR of the messenger RNA of the gene of interest makes it possible to ensure an equivalent level of transcription between the two lines to be compared.

The lines selected with puromycin thus produced are sown with equivalent confluence for semi-quantification of the expression of the product of the gene of interest using an immunoblot, by Tandem-HTRF or any other method of protein qualification by specific antibody for this protein, after lysis of the cells, then protein extraction.

A load control makes it possible to ensure the proper comparison of the equivalent total quantity of proteins between the two samples (for example, a protein of a housekeeping gene such as GAPDH, Tubulin or Actin)

Different expression levels of the protein derived from the gene of interest attest to the impact of the mutation of the Kozak sequence on the level of translation of the downstream gene with an equivalent quantity of messenger RNA attested to by the qPCR measurement done above.

It is understood that the Cyclin D1 reporter gene is used as an example and that it may be replaced by any reporter gene, such as the gene coding for Luciferase, GFP or any other marker for which the measurement of the expression is advantageous to test the impact of the Kozak sequence on the translation.

It is also understood that these traditional cloning methods can be replaced by more recent methods for assembling sequences, for example the Gibson assembly or the homologous recombination directed by CRE2 recombinase. It is for example possible to imagine placing Kozak sequences to be tested isogenically within the genome of a cell line that would have LoxP recombination sites for the CRE recombinase that would surround the Kozak sequence upstream from the desired reporter gene.

Example 3

Involvement of Cyclins in Pathologies

The impact of mutations of Kozak sequences in the Cyclin D2, Cyclin D3, Cyclin E1 and Cyclin E2 genes on the cell biology is anticipated in light of the need for Cyclin D1 for cell survival by an efficient of Caspase 3, which is a central effector of programmed cell death, said to be by apoptosis. These Cyclins are redundant in their functions during development and at adult age. For example, replacing the Cyclin D1 gene with the gene coding for Cyclin D2 or Cyclin E1 makes it possible to correct the phenotype related to the absence of Cyclin D1, which attests to this redundancy [Geng, Y. et al. Cell 97, 767-777; Carthon, B. C. et al. Mol Cell Biol 25, 1081-1088].

Based on the study of the absence of Cyclins during development (Ciemerych, M. A. & Sicinski, P. Oncogene 24, 2877-2898], a deficiency in cell protection by apoptosis inhibition owing to Cyclins D and E would result in:

1—Cyclin D1: on
neurodegenerative diseases, such as loss of dopaminergic neurons in Parkinson's disease
heart failures and myocardial infarctions associated with cell death induced by oxidative stress
nursing difficulties related to a flaw in lobuloalveolar development and/or exaggerated apoptosis of progenitors of the mammary gland
Male infertility associated with fragility on cell death by impairment of stress of germinal cells
Vision problems associated with retinal degeneration
2—Cyclin D2, on:
Problems with balance and coordination of movements related to an alteration of the homeostasis of the cerebellum
Glycemia and the appearance of diabetes due to insulin secretion defects through the beta cells of the Langerhans islets
Female infertility associated with fragility on cell death by environmental stress of the ovaries
Prostate problems associated with the loss of homeostasis of this organ with age
3—Cyclin D3, on:
infectious problems by deficiency of the immune response or loss of adaptive response with time
hyperallergic reactions or asthma symptoms
hemophilia problems
respiratory problems for lack of secretion of surfactant or loss of Club cell reservoir (also called Clara cells)
4—Cyclin E1, on:
Heart problems
5—Cyclin E2, on:
Male infertility The invention is not limited to the described embodiments, and other embodiment will appear clearly to one skilled in the art.

The invention claimed is:

1. An in vitro method for prognosis of the resistance to chemotherapy of a tumor, said method comprising
 detecting a mutation in the KOZAK sequence of the CCNDI gene by sequencing the KOZAK sequence of the CCNDI gene, said mutation being a C→G substitution in position −7 relative to the ATG codon of the sequence SEQ ID NO: 1,
 wherein the sequencing is carried out using a pair of oligonucleotides as set forth in SEQ ID NO: 38 and SEQ ID NO: 39
 and
 concluding that the tumor will be resistant to chemotherapy.

2. A method for the prognosis of resistance to chemotherapy of a tumor developed by an individual comprising:
 identifying a mutation in the KOZAK sequence of a gene coding for a Cyclin D1 protein by sequencing the KOZAK sequence of the gene, wherein the sequencing is carried out using a pair of oligonucleotides allowing sequencing of the KOZAK sequence of the gene coding the Cyclin D1 protein wherein the pair of oligonucleotides is a pair of oligonucleotides as set forth in SEQ ID NO: 38 and SEQ ID NO: 39; and,
 concluding that the tumor developed by the individual will be resistant to chemotherapy.

* * * * *

SEQUENCE LISTING

<160> NUMBER OF SEQ ID NOS: 54

<210> SEQ ID NO 1
<211> LENGTH: 27

```
<212> TYPE: DNA
<213> ORGANISM: Artificial Sequence
<220> FEATURE:
<223> OTHER INFORMATION: wild type cycline D1 Kozak sequence

<400> SEQUENCE: 1
agagccccag ccatggaaca ccagctc                                              27

<210> SEQ ID NO 2
<211> LENGTH: 27
<212> TYPE: DNA
<213> ORGANISM: Artificial Sequence
<220> FEATURE:
<223> OTHER INFORMATION: wild type Kozak cyclin D2

<400> SEQUENCE: 2
gccgggctgg ccatggagct gctgtgc                                              27

<210> SEQ ID NO 3
<211> LENGTH: 27
<212> TYPE: DNA
<213> ORGANISM: Artificial Sequence
<220> FEATURE:
<223> OTHER INFORMATION: wild type kozak cyclin D3

<400> SEQUENCE: 3
cgctgcccga gtatggagct gctgtgt                                              27

<210> SEQ ID NO 4
<211> LENGTH: 46
<212> TYPE: PRT
<213> ORGANISM: Artificial Sequence
<220> FEATURE:
<223> OTHER INFORMATION: immunogenic peptide of cyclin D1

<400> SEQUENCE: 4

Gln Ile Glu Ala Leu Leu Glu Ser Ser Leu Arg Gln Ala Gln Gln Asn
1               5                   10                  15

Met Asp Pro Lys Ala Ala Glu Glu Glu Glu Glu Glu Glu Glu Glu Val
            20                  25                  30

Asp Leu Ala Cys Thr Pro Thr Asp Val Arg Asp Val Asp Ile
        35                  40                  45

<210> SEQ ID NO 5
<211> LENGTH: 27
<212> TYPE: RNA
<213> ORGANISM: Artificial Sequence
<220> FEATURE:
<223> OTHER INFORMATION: wild type kozak cyclin D1

<400> SEQUENCE: 5
agagccccag ccauggaaca ccagcuc                                              27

<210> SEQ ID NO 6
<211> LENGTH: 27
<212> TYPE: RNA
<213> ORGANISM: Artificial Sequence
<220> FEATURE:
<223> OTHER INFORMATION: wild type kozak cyclin D2

<400> SEQUENCE: 6
gccgggcugg ccauggagcu gcugugc                                              27

<210> SEQ ID NO 7
<211> LENGTH: 27
```

```
<212> TYPE: RNA
<213> ORGANISM: Artificial Sequence
<220> FEATURE:
<223> OTHER INFORMATION: wild type kozak cyclin D3

<400> SEQUENCE: 7
cgcugcccga guauggagcu gcugugu                                27

<210> SEQ ID NO 8
<211> LENGTH: 27
<212> TYPE: DNA
<213> ORGANISM: Artificial Sequence
<220> FEATURE:
<223> OTHER INFORMATION: mutated kozac cyclin D1 - hight level

<400> SEQUENCE: 8
agagcgccag ccatggaaca ccagctc                                27

<210> SEQ ID NO 9
<211> LENGTH: 15
<212> TYPE: DNA
<213> ORGANISM: Artificial Sequence
<220> FEATURE:
<223> OTHER INFORMATION: minimal mutated kozak sequence of cyclinD1 -
      low

<400> SEQUENCE: 9
ggccgcgcca tatgg                                             15

<210> SEQ ID NO 10
<211> LENGTH: 13
<212> TYPE: DNA
<213> ORGANISM: Artificial Sequence
<220> FEATURE:
<223> OTHER INFORMATION: minimal wild type kozak sequence of cyclinD1 -
      low

<400> SEQUENCE: 10
ggccgcgcca tgg                                               13

<210> SEQ ID NO 11
<211> LENGTH: 11
<212> TYPE: PRT
<213> ORGANISM: Artificial Sequence
<220> FEATURE:
<223> OTHER INFORMATION: caspase 3 peptide

<400> SEQUENCE: 11

Ser Gly Thr Asp Val Asp Ala Ala Asn Leu Arg
1               5                   10

<210> SEQ ID NO 12
<211> LENGTH: 13
<212> TYPE: PRT
<213> ORGANISM: Artificial Sequence
<220> FEATURE:
<223> OTHER INFORMATION: caspase 3 peptide

<400> SEQUENCE: 12

Ser Val Asp Ser Gly Ile Tyr Leu Asp Ser Ser Tyr Lys
1               5                   10

<210> SEQ ID NO 13
<211> LENGTH: 18
<212> TYPE: DNA
<213> ORGANISM: Artificial Sequence
<220> FEATURE:
```

<223> OTHER INFORMATION: oligonucleotide ALDO3

<400> SEQUENCE: 13
cggcactggc catattgg                                                  18

<210> SEQ ID NO 14
<211> LENGTH: 24
<212> TYPE: DNA
<213> ORGANISM: Artificial Sequence
<220> FEATURE:
<223> OTHER INFORMATION: oligonucleotide beta2 microglobulin

<400> SEQUENCE: 14
tatgctatcc agaaaacccc tcaa                                           24

<210> SEQ ID NO 15
<211> LENGTH: 20
<212> TYPE: DNA
<213> ORGANISM: Artificial Sequence
<220> FEATURE:
<223> OTHER INFORMATION: oligonucleotide GAPDH

<400> SEQUENCE: 15
ggagcgagac cccactaaca                                                20

<210> SEQ ID NO 16
<211> LENGTH: 23
<212> TYPE: DNA
<213> ORGANISM: Artificial Sequence
<220> FEATURE:
<223> OTHER INFORMATION: oligonucleotide GUS

<400> SEQUENCE: 16
gattcagata tccgagggaa agg                                            23

<210> SEQ ID NO 17
<211> LENGTH: 20
<212> TYPE: DNA
<213> ORGANISM: Artificial Sequence
<220> FEATURE:
<223> OTHER INFORMATION: oligonucleotide HPRT

<400> SEQUENCE: 17
gcagtacagc cccaaaatgg                                                20

<210> SEQ ID NO 18
<211> LENGTH: 20
<212> TYPE: DNA
<213> ORGANISM: Artificial Sequence
<220> FEATURE:
<223> OTHER INFORMATION: oligonucleotide Mrpl32

<400> SEQUENCE: 18
aggtgctggg agctgctaca                                                20

<210> SEQ ID NO 19
<211> LENGTH: 20
<212> TYPE: DNA
<213> ORGANISM: Artificial Sequence
<220> FEATURE:
<223> OTHER INFORMATION: oligonucleotide TBP

<400> SEQUENCE: 19
atcgagtccg gtagccggtg                                                20

```
<210> SEQ ID NO 20
<211> LENGTH: 28
<212> TYPE: DNA
<213> ORGANISM: Artificial Sequence
<220> FEATURE:
<223> OTHER INFORMATION: oligonucleotide tubulin

<400> SEQUENCE: 20
cttagtgaac ttctgttgtc ctccagca                                          28

<210> SEQ ID NO 21
<211> LENGTH: 20
<212> TYPE: DNA
<213> ORGANISM: Artificial Sequence
<220> FEATURE:
<223> OTHER INFORMATION: oligonucleotide murine cyclin D1

<400> SEQUENCE: 21
aggagcagaa gtgcgaagag                                                   20

<210> SEQ ID NO 22
<211> LENGTH: 20
<212> TYPE: DNA
<213> ORGANISM: Artificial Sequence
<220> FEATURE:
<223> OTHER INFORMATION: oligonucleotide human cyclin D1

<400> SEQUENCE: 22
ggcggaggag aacaaacaga                                                   20

<210> SEQ ID NO 23
<211> LENGTH: 27
<212> TYPE: DNA
<213> ORGANISM: Artificial Sequence
<220> FEATURE:
<223> OTHER INFORMATION: oligo sens Mutag-mCcnd1 T286A-

<400> SEQUENCE: 23
ggtctggcct gcgcgcccac cgacgtg                                           27

<210> SEQ ID NO 24
<211> LENGTH: 27
<212> TYPE: DNA
<213> ORGANISM: Artificial Sequence
<220> FEATURE:
<223> OTHER INFORMATION: oligonuclotide reverse Mutag-mCcnd1 T286A-

<400> SEQUENCE: 24
cacgtcggtg ggcgcgcagg ccagacc                                           27

<210> SEQ ID NO 25
<211> LENGTH: 41
<212> TYPE: DNA
<213> ORGANISM: Artificial Sequence
<220> FEATURE:
<223> OTHER INFORMATION: oligo Flag-hKoz-SNP7-hCD1-

<400> SEQUENCE: 25
gacgatgaca agggaagagc gccagccatg gaacaccagc t                           41

<210> SEQ ID NO 26
<211> LENGTH: 41
<212> TYPE: DNA
<213> ORGANISM: Artificial Sequence
<220> FEATURE:
<223> OTHER INFORMATION: oligo reverse Flag-hKoz-SNP7-hCD1-
```

<400> SEQUENCE: 26
agctggtgtt ccatggctgg cgctcttccc ttgtcatcgt c                    41

<210> SEQ ID NO 27
<211> LENGTH: 31
<212> TYPE: DNA
<213> ORGANISM: Artificial Sequence
<220> FEATURE:
<223> OTHER INFORMATION: oligo sens hKOZ-SNP-hCD1-

<400> SEQUENCE: 27
gggatccgga agagcgccag ccatggaaca c                               31

<210> SEQ ID NO 28
<211> LENGTH: 31
<212> TYPE: DNA
<213> ORGANISM: Artificial Sequence
<220> FEATURE:
<223> OTHER INFORMATION: oligo reverse oligo sens hKOZ-SNP-hCD1-

<400> SEQUENCE: 28
gtgttccatg gctggcgctc ttccggatcc c                               31

<210> SEQ ID NO 29
<211> LENGTH: 43
<212> TYPE: DNA
<213> ORGANISM: Artificial Sequence
<220> FEATURE:
<223> OTHER INFORMATION: oligo sens mKoz-mCcnd1-

<400> SEQUENCE: 29
cagtgtggtg gtacggcggc cgcgccatgg aacaccagct cct                  43

<210> SEQ ID NO 30
<211> LENGTH: 43
<212> TYPE: DNA
<213> ORGANISM: Artificial Sequence
<220> FEATURE:
<223> OTHER INFORMATION: oligo reverse mKoz-mCcnd1-

<400> SEQUENCE: 30
aggagctggt gttccatggc gcggccgccg taccaccaca ctg                  43

<210> SEQ ID NO 31
<211> LENGTH: 44
<212> TYPE: DNA
<213> ORGANISM: Artificial Sequence
<220> FEATURE:
<223> OTHER INFORMATION: oligo sens mKoz-Flag-HA-mCcnd1-

<400> SEQUENCE: 31
ccagtgtggt ggtacggcgg ccgcgccatg gactacaagg acga                 44

<210> SEQ ID NO 32
<211> LENGTH: 44
<212> TYPE: DNA
<213> ORGANISM: Artificial Sequence
<220> FEATURE:
<223> OTHER INFORMATION: oligo reverse mKoz-Flag-HA-mCcnd1-

<400> SEQUENCE: 32
tcgtccttgt agtccatggc gcggccgccg taccaccaca ctgg                 44

<210> SEQ ID NO 33
<211> LENGTH: 46

```
<212> TYPE: DNA
<213> ORGANISM: Artificial Sequence
<220> FEATURE:
<223> OTHER INFORMATION: oligo sens mKoz-AT-Flag-HA-mCcnd1-

<400> SEQUENCE: 33
ccagtgtggt ggtacggcgg ccgcgccata tggactacaa ggacga        46

<210> SEQ ID NO 34
<211> LENGTH: 46
<212> TYPE: DNA
<213> ORGANISM: Artificial Sequence
<220> FEATURE:
<223> OTHER INFORMATION: oligo reverse mKoz-AT-Flag-HA-mCcnd1-

<400> SEQUENCE: 34
tcgtccttgt agtccatatg gcgcggccgc cgtaccacca cactgg        46

<210> SEQ ID NO 35
<211> LENGTH: 34
<212> TYPE: DNA
<213> ORGANISM: Artificial Sequence
<220> FEATURE:
<223> OTHER INFORMATION: human cycD1 sequence

<400> SEQUENCE: 35
gcccaggaag agccccagcc atgggaacac cagc        34

<210> SEQ ID NO 36
<211> LENGTH: 14
<212> TYPE: DNA
<213> ORGANISM: Artificial Sequence
<220> FEATURE:
<223> OTHER INFORMATION: human cycD1 sequence

<400> SEQUENCE: 36
atgggaacac cagc        14

<210> SEQ ID NO 37
<211> LENGTH: 4
<212> TYPE: PRT
<213> ORGANISM: Artificial Sequence
<220> FEATURE:
<223> OTHER INFORMATION: N-terminus of hCycD1

<400> SEQUENCE: 37

Met Glu His Gln
1

<210> SEQ ID NO 38
<211> LENGTH: 18
<212> TYPE: DNA
<213> ORGANISM: Artificial Sequence
<220> FEATURE:
<223> OTHER INFORMATION: ccnd1 sense primer

<400> SEQUENCE: 38
gggcagcaga agcgagag        18

<210> SEQ ID NO 39
<211> LENGTH: 18
<212> TYPE: DNA
<213> ORGANISM: Artificial Sequence
<220> FEATURE:
<223> OTHER INFORMATION: ccnd1 antisense primer

<400> SEQUENCE: 39
```
cggtcgttga ggaggttg                                                    18

<210> SEQ ID NO 40
<211> LENGTH: 20
<212> TYPE: DNA
<213> ORGANISM: Artificial Sequence
<220> FEATURE:
<223> OTHER INFORMATION: ccnd2 sense primer

<400> SEQUENCE: 40
tagccaaagg aaggaggtca                                                  20

<210> SEQ ID NO 41
<211> LENGTH: 20
<212> TYPE: DNA
<213> ORGANISM: Artificial Sequence
<220> FEATURE:
<223> OTHER INFORMATION: ccnd2 reverse primer

<400> SEQUENCE: 41
aagtaggagc actgcggaag                                                  20

<210> SEQ ID NO 42
<211> LENGTH: 20
<212> TYPE: DNA
<213> ORGANISM: Artificial Sequence
<220> FEATURE:
<223> OTHER INFORMATION: ccnd3 sense primer

<400> SEQUENCE: 42
attccacggt tgctacatcg                                                  20

<210> SEQ ID NO 43
<211> LENGTH: 20
<212> TYPE: DNA
<213> ORGANISM: Artificial Sequence
<220> FEATURE:
<223> OTHER INFORMATION: ccnd3 reverse primer

<400> SEQUENCE: 43
gcacgcactg gaagtaggag                                                  20

<210> SEQ ID NO 44
<211> LENGTH: 21
<212> TYPE: DNA
<213> ORGANISM: Artificial Sequence
<220> FEATURE:
<223> OTHER INFORMATION: siRNA against ccnd1

<400> SEQUENCE: 44
gccaggatga taagttcctt t                                                21

<210> SEQ ID NO 45
<211> LENGTH: 20
<212> TYPE: DNA
<213> ORGANISM: Artificial Sequence
<220> FEATURE:
<223> OTHER INFORMATION: siRNA against ccnd1

<400> SEQUENCE: 45
attggaatag cttctggaat                                                  20

<210> SEQ ID NO 46
<211> LENGTH: 21
<212> TYPE: DNA

```
<213> ORGANISM: Artificial Sequence
<220> FEATURE:
<223> OTHER INFORMATION: siRNA against ccnd1

<400> SEQUENCE: 46
ccacagatgt gaagttcatt t                                              21

<210> SEQ ID NO 47
<211> LENGTH: 16
<212> TYPE: DNA
<213> ORGANISM: Artificial Sequence
<220> FEATURE:
<223> OTHER INFORMATION: wild type cycline E1 Kozak sequence

<400> SEQUENCE: 47
agccccatca tgccga                                                    16

<210> SEQ ID NO 48
<211> LENGTH: 18
<212> TYPE: DNA
<213> ORGANISM: Artificial Sequence
<220> FEATURE:
<223> OTHER INFORMATION: wild type cycline E2 Kozak sequence

<400> SEQUENCE: 48
aagaagagaa tgtcaaga                                                  18

<210> SEQ ID NO 49
<211> LENGTH: 16
<212> TYPE: RNA
<213> ORGANISM: Artificial Sequence
<220> FEATURE:
<223> OTHER INFORMATION: wild type kozak cyclin E1

<400> SEQUENCE: 49
agccccauca ugccga                                                    16

<210> SEQ ID NO 50
<211> LENGTH: 18
<212> TYPE: RNA
<213> ORGANISM: Artificial Sequence
<220> FEATURE:
<223> OTHER INFORMATION: wild type kozak cyclin E2

<400> SEQUENCE: 50
aagaagagaa ugucaaga                                                  18

<210> SEQ ID NO 51
<211> LENGTH: 18
<212> TYPE: DNA
<213> ORGANISM: Artificial Sequence
<220> FEATURE:
<223> OTHER INFORMATION: ccne1 forward primer

<400> SEQUENCE: 51
ggacaagacc ctggcctc                                                  18

<210> SEQ ID NO 52
<211> LENGTH: 20
<212> TYPE: DNA
<213> ORGANISM: Artificial Sequence
<220> FEATURE:
<223> OTHER INFORMATION: ccne1 reverse primer

<400> SEQUENCE: 52
gtcctgtcga ttttggccat                                                20
```

```
<210> SEQ ID NO 53
<211> LENGTH: 20
<212> TYPE: DNA
<213> ORGANISM: Artificial Sequence
<220> FEATURE:
<223> OTHER INFORMATION: ccne2 forward primer

<400> SEQUENCE: 53
ctttgttccc ggagctgttc                                              20

<210> SEQ ID NO 54
<211> LENGTH: 20
<212> TYPE: DNA
<213> ORGANISM: Artificial Sequence
<220> FEATURE:
<223> OTHER INFORMATION: ccne2 reverse primer

<400> SEQUENCE: 54
tttcctcttc ttggcctgga                                              20
```